US011707455B2

(12) United States Patent
Dong et al.

(10) Patent No.: US 11,707,455 B2
(45) Date of Patent: Jul. 25, 2023

(54) PHARMACEUTICAL COMPOSITION CONTAINING DABIGATRAN ETEXILATE AND PREPARATION METHOD THEREOF

(71) Applicant: SHANGHAI WD PHARMACEUTICAL CO., LTD, Shanghai (CN)

(72) Inventors: Liang Chang Dong, Shanghai (CN); Shizhong Zhang, Shanghai (CN); Yan Jiao, Shanghai (CN); Danyong Zhang, Shanghai (CN); Wenfang Zhao, Shanghai (CN); Jingmin Shi, Shanghai (CN)

(73) Assignee: SHANGHAI WD PHARMACEUTICAL CO., LTD, Shanghai (CN)

( * ) Notice: Subject to any disclaimer, the term of this patent is extended or adjusted under 35 U.S.C. 154(b) by 144 days.

(21) Appl. No.: 17/043,442

(22) PCT Filed: Nov. 27, 2018

(86) PCT No.: PCT/CN2018/117619
§ 371 (c)(1),
(2) Date: Sep. 29, 2020

(87) PCT Pub. No.: WO2019/192195
PCT Pub. Date: Oct. 10, 2019

(65) Prior Publication Data
US 2021/0369695 A1 Dec. 2, 2021

(30) Foreign Application Priority Data

Apr. 4, 2018 (CN) .......................... 201810300259.6

(51) Int. Cl.
| | | |
|---|---|---|
| A61K 31/4439 | (2006.01) | |
| A61K 9/16 | (2006.01) | |
| A61K 47/10 | (2017.01) | |
| A61K 47/12 | (2006.01) | |
| A61K 47/26 | (2006.01) | |
| A61K 47/32 | (2006.01) | |
| A61K 47/38 | (2006.01) | |

(52) U.S. Cl.
CPC ........ *A61K 31/4439* (2013.01); *A61K 9/1694* (2013.01); *A61K 47/10* (2013.01); *A61K 47/12* (2013.01); *A61K 47/26* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 8,962,574 | B2 | 2/2015 | Reilly |
| 2011/0224441 | A1* | 9/2011 | Lustig ................. C07D 401/12 |
| | | | 546/273.4 |
| 2013/0052262 | A1 | 2/2013 | Brueck et al. |
| 2013/0149346 | A1 | 6/2013 | Meergans et al. |
| 2014/0302150 | A1 | 10/2014 | Cifter et al. |
| 2014/0322338 | A1 | 10/2014 | Cifter et al. |
| 2015/0030680 | A1 | 1/2015 | Pilgaonkar et al. |
| 2015/0366807 | A1 | 12/2015 | Krekeler et al. |
| 2015/0366813 | A1 | 12/2015 | Thakur et al. |

FOREIGN PATENT DOCUMENTS

| | | | |
|---|---|---|---|
| CN | 104644543 | A | 5/2015 |
| CN | 106880845 | * | 12/2015 |
| CN | 105997868 | * | 6/2016 |
| CN | 105997868 | A | 10/2016 |
| CN | 106880845 | * | 6/2017 |
| CN | 106880845 | A | 6/2017 |
| CN | 110339193 | A | 10/2019 |
| WO | 03/074056 | A | 9/2003 |
| WO | WO-2015/071841 | A1 | 5/2015 |

OTHER PUBLICATIONS

Kendre et al. (Effect of polyvinyl caprolactam-polyvinyl acetate-polyethylene glycol graft copolymer on bio adhesion and release rate property of eplerenone pellets, Drug Development and Industrial Pharmacy, 43:5, 751-761; published online Aug. 25, 2016) (Year: 2016).*
Second Office Action dated Jan. 17, 2022 issued in CN Application No. 201810300259.6, with English translation, 8 pages.
Notice of Reasons for Refusal dated Oct. 5, 2021 issued in Japanese Patent Application No. 2020-554215, with English translation, 10 pages.
International Search Report dated Mar. 11, 2019 issued in International Patent Application No. PCT/CN2018/117619, with English translation, 7 pages.
Written Opinion of the International Searching Authority dated Mar. 11, 2019 issued in International Patent Application No. PCT/CN2018/117619, with English translation, 7 pages.
Wu, Huimin, et al., "Applications of Soluplus to Pharmaceutical Formulations," Chinese Journal of Pharmaceuticals, vol. 47, No. 4, 2016, ISSN: 1001-8255, pp. 478-483, with English translation.

(Continued)

*Primary Examiner* — Melissa S Mercier
(74) *Attorney, Agent, or Firm* — Foley & Lardner LLP

(57) ABSTRACT

Disclosed is a pharmaceutical composition containing dabigatran etexilate and a preparation method thereof. The pharmaceutical composition comprises a pharmaceutically active ingredient, dabigatran etexilate and/or dabigatran etexilate mesylate, and a amphiphilic polymer of polyvinyl caprolactam-polyvinyl acetate-polyethylene glycol graft copolymer. The mass ratio of the two is 1:0.23 to 1:3. The pharmaceutical composition not only increases the bioavailability of the pharmaceutically active ingredient, but also reduces absorption variability, and provides a more stable concentration of dabigatran in plasma, thereby reducing adverse side effects.

18 Claims, 13 Drawing Sheets

(56) References Cited

OTHER PUBLICATIONS

Cohen, Deborah, "Dabigatran: how the drug company withheld important analyses," BMJ 2014;349:g4670, (published Jul. 23, 2014), doi: 10.1136/bmj.g4670, 7 pages.

BASF: "Soluplus—Technical information," Internet Citation, Jul. 2010, pp. 1-8, XP002666808, retrieved from the internet: URL: http://www.pharma-ingredients.basf.com/Statements/Technical%20Informations/EN/Pharma%20Solutions/03_090801eSoluplus.pdf.

Benes, M., et al., "Application of Spectroscopic Imaging for Characterizing API: Polymer Systems as a Screening Tool for the Development of Potential Amorphous Solid Dispersions," Acta Poloniae Pharmaceutica N Drug Research, vol. 74, No. 6, 2017, pp. 1851-1858, XP055797083.

First Office Action dated Jun. 2, 2021 issued in CN Application No. 201810300259.6, with English translation, 10 pages.

Hu, Mei, et al., "Improved oral bioavailability and therapeutic efficacy of dabigatran etexilate via Soluplus-TPGS binary mixed micelles system," Drug Development and Industrial Pharmacy, 2017, vol. 43, No. 4, pp. 687-697, http://dx.doi.org/10.1080/03639045.2016.1278015.

Punčochová, Kateřina, et al., "The impact of polymeric excipients on the particle size of poorly soluble drugs after pH-induced precipitation," 2016, Accepted Manuscript, DOI: 10.1016/j.ejps.2016.08.028.

Extended European Search Report dated Apr. 30, 2021 issued in EP Application No. 18913737.5, 10 pages.

First Office Action dated Feb. 18, 2023 issued in CN Patent Application No. 201880091596.7, with English translation, 13, pages.

* cited by examiner

PHARMACEUTICAL COMPOSITION CONTAINING DABIGATRAN ETEXILATE AND PREPARATION METHOD THEREOF

CROSS-REFERENCE TO RELATED APPLICATIONS

The present application is a 371 of PCT/CN2018/117619, filed Nov. 27, 2018, which is based upon and claims priority to Chinese patent application CN201810300259.6 filed on Apr. 4, 2018, both of which are hereby incorporated by reference in their entireties.

FIELD OF INVENTION

The present disclosure relates to a pharmaceutical composition containing dabigatran etexilate and a preparation method thereof.

PRIOR ARTS

The chemical name of dabigatran etexilate mesylate (DEM) is β-alanine, N-[[2-[[[4-[[(hexyloxy)carbonyl]amino]iminomethyl]phenyl]amino]methyl]-1-methyl-1H-benzimidazole-5-yl]carbonyl]-N-2-pyridyl-ethyl ester methanesulfonate, an empirical formula is $C_{34}H_{41}N_7O_5 \cdot CH_4O_3S$, the molecular weight is 723.86, and CAS # is 872728-81-9. A structural formula of the DEM is:

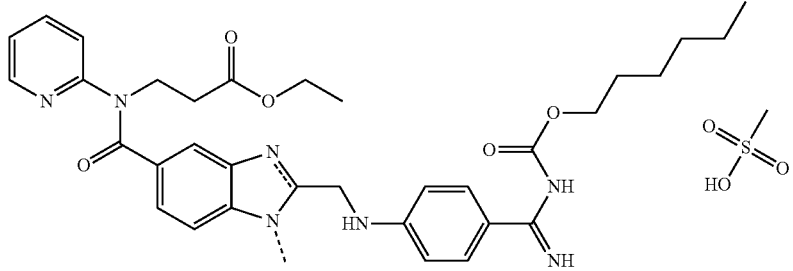

The DEM is an active pharmaceutical ingredient (API) of a commodity Pradaxa capsule, is a pro-drug of dabigatran and is a direct inhibitor of thrombin. The Pradaxa capsule is sold by Boehringer Ingelheim GmbH, and the Pradaxa capsule is utilized to lower the risk of stroke and thrombus of atrial fibrillation patients caused by non-cardiac valve issues, and also utilized to treat deep venous thrombosis and pulmonary embolism.

The DEM is white to faint-yellow powder. The DEM is freely soluble in methanol, sparingly soluble in isopropanol and slightly soluble in ethanol. A saturated solution of the DEM in pure water has the solubility of 1.8 mg/mL. The DEM has pH-dependent solubility distribution, the maximum solubility is greater than 80 mg/mL when pH is 1, and the DEM is insoluble under neutral pH. The poor solubility of the DEM under neutral pH is the culprit of its low and erratic oral absorption.

Various methods aiming at improving DEM dissolution are disclosed in the prior art.

US Patent applications 20130052262 and 20150366807 discloses a pharmaceutical preparation composed of DEM and an inorganic acid. The inorganic acid in the pharmaceutical preparation may increase solubility in gastric fluid, but the problem of precipitation of the DEM in neutral media is still not solved.

A pharmaceutical composition disclosed in a US patent application 20150030680 contains two types of granules, one type of the granules contains DEM, and the other type of granules contains an organic acid. The organic acid in the pharmaceutical preparation may increase solubility in gastric fluid, but the problem of precipitation of the DEM in neutral media is still not solved.

A lipophilic pharmaceutical composition disclosed in a US patent application 20150366813 contains easily-hydrolysed APIs such as DEM, and the APIs are suspended in the pharmaceutical composition, so that the APIs are prevented from making contact with water and thus dissolution of the APIs is increased. However, the pharmaceutical composition disclosed in the patent application still cannot solve the problem of precipitation of the DEM in neutral media.

A US patent application 20130149346A1 discloses a DEM solid solution composition using polyethylene glycols, polyethylene glycol glycerides, block-copolymers of ethylene oxide and propylene oxide, as well as hydroxypropyl methyl cellulose and polyvinylpyrrolidone as solid solvents. The patent application does not show dissolution profile under neutral pH, and therefore whether the DEM dissolution of the solid solutions is increased or not cannot be confirmed.

A preparation is disclosed in WO03/074056, which enables DEM to be immediately released through tartaric acid to improve the dissolution of the DEM in gastrointestinal tracts. As described above, the method is suitable for the situation that the pH value of gastric fluid is artificially increased by administrating a proton pump inhibitor Pantoprazole. The pharmaceutical composition is called as a commercially-available product Pradaxa, and is prepared through the following method: spraying a sealing layer composition onto the surfaces of tartaric acid cores, and then spraying a DEM and a film forming agent suspension liquid onto the sealed tartaric acid cores. A sealing layer is utilized to prevent interaction between the DEM and tartaric acid. Due to a high ratio of an API to a polymer film forming agent, the DEM mainly exists in the form of crystals, and thus a dissolution profile of the DEM is strongly dependent to pH. Compared with a preparation without tartaric acid, the oral bioavailability of the Pradaxa is improved but is still low and is about 3 to 7%. In addition, when a pill without a hydroxypropyl methyl cellulose (HPMC) capsule shell is orally taken, the oral bioavailability of the Pradaxa is increased by 75%, representing that the percentage of the DEM dissolved in gastric fluid will be lowered by slow dissolution of an HPMC capsule, and consequently the bioavailability of the DEM is lowered.

Even the DEM is easily dissolved in gastric fluid under the action of tartaric acid, the dissolved DEM may precipitate after being emptied from the stomach to the small intestine, and thus absorption of the DEM is lowered. In addition, "Dabigatran: how the drug company withheld important analyses (Deborah Cohen, investigations editor, The BMJ, BMJ 2014; 349)" indicates that use of tartaric acid to enhance DEM's solubility in the GIT fluid leads to large variability in DEM absorption, with the $C_{max}$ ranging as high as 5 folds Due to the low therapeutic index of the DEM, $C_{max}$ with the excessively-wide variation range may further cause harmful side effects, such as massive hemorrhage. In order to relieve potential massive hemorrhage caused by high plasma DEM concentration, a low dosage strength of 110 mg is adopted in a U.S. Pat. No. 8,962,574 to replace 150 mg.

CONTENT OF THE PRESENT INVENTION

In view of the technical problems to be solved, the present disclosure aims to overcome the defect that in the prior art, a medicinal preparation containing dabigatran etexilate is prone to being precipitated in intestinal fluid, and the present disclosure provides a pharmaceutical composition containing dabigatran etexilate and a preparation method thereof. A dissolution profile of the pharmaceutical composition is less affected by pH of gastrointestinal fluid, precipitation of DEM in neutral-pH intestinal fluid may further be avoided, and thus the pharmaceutical composition may enhance oral absorption of the dabigatran etexilate or pharmaceutically acceptable salts thereof, improve bioavailability of an API, further lower absorption variability and meanwhile provide a more stable concentration of dabigatran in plasma, thereby reducing adverse side effects and possibility of GIT hemorrhage. In addition, due to absorption enhancement, non-absorbed DEM in gastrointestinal tracts is remarkably reduced, thus further relieving GIT massive hemorrhage. When the API and other components of the pharmaceutical composition jointly form solid dispersion, all the DEM is pre-dissolved in a carrier (the carrier is other components except the API), saving the worry about dissolution of drugs. The carrier may quickly dissolve out under conditions of aqueous media and acid pH, so possibility of DEM recrystallization may be reduced and even eliminated, and therefore DEM absorption is further promoted.

The present disclosure solves the technical problem through following technical solutions:

The present disclosure provides a pharmaceutical composition containing dabigatran etexilate, and the pharmaceutical composition includes an active pharmaceutical ingredient and an amphiphilic polymer, wherein the active pharmaceutical ingredient is dabigatran etexilate and/or DEM, the amphiphilic polymer is polyvinyl caprolactam-polyvinyl acetate-polyethylene glycol graft copolymer, and a mass ratio of the active pharmaceutical ingredient to the amphiphilic polymer is 1:0.23 to 1:3.

In the present disclosure, preferably, the active pharmaceutical ingredient is dabigatran etexilate or dabigatran etexilate mesylate.

In the present disclosure, the mass of the active pharmaceutical ingredient in the pharmaceutical composition is preferably 30 to 180 mg, and more preferably 39.1 to 173 mg.

In the present disclosure, the number of repeat units of vinyl caprolactam in the amphiphilic polymer is preferably 57 or below. The number of repeat units of vinyl acetate in the amphiphilic polymer is preferably 30 or below. The number of repeat units of polyethylene glycol in the amphiphilic polymer is preferably 13 or above. In the amphiphilic polymer, vinyl caprolactam units account for preferably 57%, vinyl acetate units account for preferably 30%, polyethylene glycol units account for preferably 13%, and the percentages are mole percentages. The polyethylene glycol is preferably polyethylene glycol 6000. Monomers of the amphiphilic polymer are preferably polyethylene glycol 6000, vinyl caprolactam and vinyl acetate. A mole ratio of the three repeat units, namely the polyethylene glycol 6000, the vinyl caprolactam and the vinyl acetate, in the amphiphilic polymer is preferably 13:57:30. A molecular weight of the amphiphilic polymer is preferably 90,000 to 140,000 g/mol. A glass-transition temperature of the amphiphilic polymer is preferably 69 to 71° C. The amphiphilic polymer is more preferably Soluplus®, and the Soluplus® is a commercially available product with a manufacturer being BASF SE. The Soluplus® is polyvinyl caprolactam-polyvinyl acetate-polyethylene glycol graft copolymer; the number of repeat units of vinyl caprolactam in the Soluplus® is 57 or below, the number of repeat units of vinyl acetate in the Soluplus® is 30 or below, and the number of repeat units of polyethylene glycol in the Soluplus® is 13 or above; and the repeat units of the amphiphilic polymer are the polyethylene glycol 6000, the vinyl caprolactam and the vinyl acetate, the mole ratio of the three units, namely the polyethylene glycol 6000, the vinyl caprolactam and the vinyl acetate is 13:57:30, a molecular weight of the Soluplus® is 90,000 to 140,000 g/mol (such as 118,000 g/mol), and a glass-transition temperature of the Soluplus® is about 70° C.

In the present disclosure, the mass ratio of the active pharmaceutical ingredient to the amphiphilic polymer is preferably 1:0.24 to 1:3, 1:0.3 to 1:3, 1:0.5 to 1:3, 1:1.5 to 1:3 or 1:1.5 to 1:2.3, such as 1:0.24, 1:0.25, 1:0.33, 1:0.77, 1:1, 1:1.2, 1:1.5, 1:1.6, 1:2 or 1:2.3.

In the present disclosure, the pharmaceutical composition may further include a hydrophilic polymer, and the hydrophilic polymer may be a water-soluble material conventionally used in the art.

Wherein, a mass ratio of the active pharmaceutical ingredient to the hydrophilic polymer is preferably 1:0.45 to 1:4, and more preferably 1:0.5 to 1:3, such as 1:1.2, 1:1.25, 1:1.9, 1:2, 1:2.5 or 1:2.85.

The hydrophilic polymer is preferably one or more selected from the group consisting of polyoxyethylene-polyoxypropylene glycol block copolymer, polyvinylpyrrolidone, polyvinylpyrrolidone-co-vinyl acetate, methyl cellulose, hydroxypropyl cellulose, hydroxyethyl cellulose, hydroxypropyl methyl cellulose and polyacrylate. It needs to be stated herein that the polyoxyethylene-polyoxypropylene glycol block copolymer is a copolymer formed by polyethylene glycol and polypropylene glycol, and is preferably Kolliphor® P188 and/or Kolliphor® P407. The polyvinylpyrrolidone is preferably PVP K12. The polyvinylpyrrolidone-co-vinyl acetate is preferably Kollidon® VA64 (Acetic acid ethenyl ester, polymer with 1-ethenyl-2-pyrrolidinone). The hydroxypropyl cellulose is preferably Klucel™ EF (Cellulose, 2-hydroxypropyl ether). The hydroxypropyl methyl cellulose is preferably HPMC E5 and/or HPMC VLV. The polyacrylate is preferably Eudragit® L100 (Poly(methacrylic acid, methyl methacrylate) 1:1).

When the pharmaceutical composition includes the hydrophilic polymer, a mass percentage of the active pharmaceutical ingredient in the pharmaceutical composition may be conventional in the art, for example, 5 wt % to 60 wt %, preferably 10 wt % to 55 wt %, and more preferably 20 wt % to 45 wt %, such as 13.3 wt %, 14.4 wt %, 16.9 wt %, 17.0 wt %, 18.0 wt %, 24.0 wt %, 39.1 wt % or 43.4 wt %.

When the pharmaceutical composition includes the hydrophilic polymer, a mass percentage of the amphiphilic polymer in the pharmaceutical composition is preferably 3 wt % to 40 wt %, such as 3.3 wt %, 6.0 wt %, 9.2 wt %, 10.0 wt %, 12.8 wt %, 12.9 wt %, 18.6 wt %, 21.3 wt %, 22.5 wt %, 22.8 wt %, 24.3 wt %, 28.3 wt %, 38.8 wt % or 39.2 wt %.

When the pharmaceutical composition includes the hydrophilic polymer, a mass percentage of the hydrophilic polymer in the pharmaceutical composition may be conventional in the art, for example, 10 wt % to 90 wt %, preferably 20 wt % to 80 wt %, and more preferably 40 wt % to 60 wt %, such as 16.7 wt %, 19.2 wt %, 19.9 wt %, 22.2 wt %, 26.1 wt %, 27.4 wt %, 29.6 wt %, 31.0 wt %, 33.3 wt %, 35.9 wt %, 30.0 wt % or 36.0 wt %.

The above hydrophilic polymer may enhance dissolution of the active pharmaceutical ingredient in the pharmaceutical composition under acid pH, and further potential recrystallization of the active pharmaceutical ingredient dispersed in the pharmaceutical composition in the form of molecules is lowered to the minimum.

In the present disclosure, the pharmaceutical composition may further include a disintegrating agent conventionally used in the art, and the disintegrating agent is preferably one or more selected from the group consisting of croscarmellose sodium, low-substituted hydroxypropyl cellulose, sodium starch glycolate and crospovidone, and more preferably the croscarmellose sodium and/or the low-substituted hydroxypropyl cellulose.

Wherein, a mass percentage of the disintegrating agent in the pharmaceutical composition may be conventional in the art, for example, 0 wt % to 5 wt %, but not 0 wt %, and preferably 3 wt % to 5 wt %.

In the present disclosure, the pharmaceutical composition may further include an antistatic agent conventionally used in the art, and the antistatic agent is preferably one or more selected from the group consisting of long-chained alkylphenol, ethoxylated amine, glyceride and silica, and more preferably the silica.

Wherein, a mass percentage of the antistatic agent in the pharmaceutical composition may be conventional in the art, for example 0 wt % to 5 wt %, but not 0 wt %, preferably 0.01 wt % to 3 wt %, and more preferably 0.5 wt % to 2 wt %. The addition of the antistatic agent is beneficial to spraying and encapsulating of the pharmaceutical composition.

In the present disclosure, the pharmaceutical composition may further include a lubricant (also called as a glidant) conventionally used in the art, and the lubricant is preferably one or more selected from the group consisting of calcium stearate, glyceryl behenate, magnesium stearate, sodium stearyl fumarate, talcum powder, colloidal silica, magnesium silicate and calcium silicate, and more preferably the magnesium stearate.

Wherein, amass percentage of the lubricant in the pharmaceutical composition may be conventional in the art, for example, 0 wt % to 5 wt %, but not 0 wt %, preferably 0.01 wt % to 3 wt %, and more preferably 0.5 wt % to 2 wt %. The addition of the lubricant is beneficial to spray-drying or spraying of the pharmaceutical composition, and filling of capsules with solid granules or pellets containing the pharmaceutical composition.

In present disclosure, the pharmaceutical composition may further include a diluent conventionally used in the art, and the diluent is preferably mannitol and/or lactose monohydrate.

Wherein, a mass percentage of the diluent in the pharmaceutical composition may be conventional in the art, for example, 0 wt % to 40 wt %, but not 0 wt %, and preferably 9 wt % to 38.3 wt %.

In the present disclosure, preferably, the pharmaceutical composition includes the components of following mass fraction: 9% to 48% of the active pharmaceutical ingredient, 9% to 44% of the amphiphilic polymer, 0% to 53% of the hydrophilic polymer, 0% to 90% of the diluent, 0% to 20% of the disintegrating agent, 0% to 5% of the antistatic agent and 0% to 2% of the lubricant. More preferably, the pharmaceutical composition includes the components of following mass fraction: 9% to 48% of the dabigatran etexilate mesylate, 9% to 44% of Soluplus®, 0% to 30% of Kolliphor® P407, 0% to 23% of Kolliphor® P188, 0% to 58% of lactose monohydrate, 0% to 32% of mannitol, 0% to 20% of croscarmellose sodium, 0% to 5% of silica and 0% to 3% of magnesium stearate.

In the present disclosure, preferably, the pharmaceutical composition includes the components of following mass fraction: 13% to 44% of the active pharmaceutical ingredient, 6% to 39% of the amphiphilic polymer, 16% to 36% of the hydrophilic polymer, 9% to 39% of the diluent, 5% to 23% of the disintegrating agent and 0.4% to 0.5% of the lubricant. The active pharmaceutical ingredient is preferably the dabigatran etexilate mesylate. The amphiphilic polymer is preferably Soluplus®. The hydrophilic polymer is preferably Kolliphor® P407 and/or Kolliphor® P188. The diluent is preferably lactose monohydrate and/or mannitol. The disintegrating agent is preferably the croscarmellose sodium and/or the low-substituted hydroxypropyl cellulose. The lubricant is preferably the magnesium stearate.

In the present disclosure, preferably, the pharmaceutical composition includes the components of following mass fraction: 16% to 19% of the active pharmaceutical ingredient, 21% to 43% of the amphiphilic polymer, 32% to 58% of the diluent, 5% to 20% of the disintegrating agent and 0% to 2% of the lubricant. More preferably, the pharmaceutical composition includes the components of following mass fraction: 16% to 19% of dabigatran etexilate mesylate, 21% to 43% of Soluplus®, 32% to 58% of lactose monohydrate, 5% to 20% of croscarmellose sodium and 0% to 2% of magnesium stearate.

In the present disclosure, preferably, the pharmaceutical composition includes the components of following mass fraction: 16% to 18% of the active pharmaceutical ingredient, 26% to 44% of the amphiphilic polymer, 17% to 23% of the hydrophilic polymer, 0% to 32% of the diluent, 5% to 20% of the disintegrating agent and 0% to 2% of the lubricant. More preferably, the pharmaceutical composition includes the components of following mass fraction: 16% to 18% of dabigatran etexilate mesylate, 26% to 44% of Soluplus®, 0% to 32% of mannitol, 17% to 23% of Kolliphor® P188, 5% to 20% of croscarmellose sodium and 0% to 2% of magnesium stearate.

In a preferred embodiment of the present disclosure, the pharmaceutical composition is composed of the components of following mass fraction: 17% of the dabigatran etexilate mesylate, 39.2% of Soluplus®, 38.3% of lactose monohydrate, 5.0% of croscarmellose sodium and 0.5% of magnesium stearate.

In a preferred embodiment of the present disclosure, the pharmaceutical composition is composed of the components of following mass fraction: 16.9% of dabigatran etexilate mesylate, 38.8% of Soluplus®, 18.9% of mannitol, 19.9% of Kolliphor® P188, 5.0% of croscarmellose sodium and 0.5% of magnesium stearate.

In a preferred embodiment of the present disclosure, the pharmaceutical composition is composed of the components of following mass fraction: 43.35% of dabigatran etexilate mesylate, 10% of Soluplus®, 9% of mannitol, 22.15% of Kolliphor® P407, 15.0% of croscarmellose sodium and 0.5% of magnesium stearate.

In a preferred embodiment of the present disclosure, the pharmaceutical composition is composed of the components of following mass fraction: 43.35% of dabigatran etexilate mesylate, 10% of Soluplus®, 9% of mannitol, 22.15% of Kolliphor® P407, 15.0% of low-substituted hydroxypropyl cellulose and 0.5% of magnesium stearate.

In a preferred embodiment of the present disclosure, the pharmaceutical composition is composed of the components of following mass fraction: 39.1% of dabigatran etexilate mesylate, 9.2% of Soluplus®, 9.2% of mannitol, 19.2% of Kolliphor® P188, 23.0% of croscarmellose sodium and 0.4% of magnesium stearate.

In the present disclosure, the pharmaceutical composition described above generally exists in the following forms: powder, pellets, granules, capsules or tablets, in the dosage forms, the active pharmaceutical ingredient and other components in the pharmaceutical composition may jointly form a solid dispersion, and the active pharmaceutical ingredient and the other components in the pharmaceutical composition may further be physically mixed to form a uniformly-mixed system.

When the pharmaceutical composition exists in the form of powder, the active pharmaceutical ingredient and the other components in the pharmaceutical composition jointly form a solid dispersion, and a method for preparing the powder may be a conventional preparation method in the art, for example, all the components of the pharmaceutical composition are dissolved in an organic solvent and spray-drying is carried out. Preferably, the method for preparing the powder includes the following steps: dissolving all the components of the pharmaceutical composition in an ethanol aqueous solution, and carrying out spray-drying, wherein a mass fraction of ethanol in the ethanol aqueous solution is 90% to 95%. In the powder, the active pharmaceutical ingredient existing in a molecular dispersion form and/or an amorphous form may account for 15 wt % to 100 wt % of total mass of the active pharmaceutical ingredient, preferably 40 wt % to 100 wt %, and more preferably 60 wt % to 100 wt %.

The pellet is provided with a core and a drug layer wrapping the core, the drug layer is a solid dispersion layer which is jointly formed by all the components of the pharmaceutical composition to wrap the core, and the pellet may be divided into a neutral-core pellet and an acid-core pellet according to the difference of pH value of solution formed by the core.

When the pharmaceutical composition exists in the form of the neutral-core pellet, the neutral-core pellet are provided with a neutral core and a drug layer wrapping the neutral core, the drug layer is a solid dispersion layer which is jointly formed by all the components of the pharmaceutical composition to wrap the neutral core, and the neutral-core pellet include the components of following mass fraction: 9% to 30% of the active pharmaceutical ingredient, 2% to 24% of the amphiphilic polymer, 11% to 42% of the hydrophilic polymer and 33% to 77% of the neutral core.

Wherein, the active pharmaceutical ingredient existing in a molecular dispersion form and/or an amorphous form may account for 15 wt % to 100 wt % of total mass of the active pharmaceutical ingredient, preferably 40 wt % to 100 wt %, and more preferably 60 wt % to 100 wt %.

Wherein, the neutral core may be a neutral core conventionally used in the art for preparing a neutral-core pellet, such as microcrystalline cellulose core and/or sugar spheres. Preferably, the neutral core is sugar spheres.

Wherein, preferably, the neutral-core pellet comprises the components of following mass fraction: 12% to 30% of the active pharmaceutical ingredient, 6% to 24% of the amphiphilic polymer, 15% to 42% of the hydrophilic polymer and 33% to 50% of the neutral cores. More preferably, the neutral-core pellet comprises the components of following mass fraction: 12% to 30% of dabigatran etexilate mesylate, 6% to 24% of Soluplus®, 15% to 42% of Kolliphor® P407 and 33% to 50% of sugar spheres.

Wherein, preferably, the neutral-core pellet comprises the components of following mass fraction: 9% to 20% of the active pharmaceutical ingredient, 2% to 5% of the amphiphilic polymer, 11% to 25% of the hydrophilic polymer and 50% to 77% of the neutral core. More preferably, the neutral-core pellet comprises the components of following mass fraction: 9% to 20% of dabigatran etexilate mesylate, 2% to 5% of Soluplus®, 11% to 25% of Kolliphor® P407 and 50% to 77% of sugar spheres.

Wherein, preferably, the neutral-core pellet comprises the following components of following mass fraction: 13.3% to 24% of the active pharmaceutical ingredient, 3.33% to 28.27% of the amphiphilic polymer, 16.7% to 36% of the hydrophilic polymer and 40% to 66.7% of the neutral core. The active pharmaceutical ingredient is preferably dabigatran etexilate mesylate. The amphiphilic polymer is preferably Soluplus®. The hydrophilic polymer is preferably Kolliphor® P407 and/or Kolliphor® P188. The neutral core is sugar spheres and/or microcrystalline cellulose core.

In a preferred embodiment of the present disclosure, the pharmaceutical composition is composed of the following components in percentage by mass: 18% of dabigatran etexilate mesylate, 6% of Soluplus®, 36% of Kolliphor® P407 and 40% of sugar spheres.

In a preferred embodiment of the present disclosure, the pharmaceutical composition is composed of the components of following mass fraction: 24% of dabigatran etexilate mesylate, 6% of Soluplus®, 30% of Kolliphor® P407 and 40% of sugar spheres.

In a preferred embodiment of the present disclosure, the pharmaceutical composition is composed of the components of following mass fraction: 13.3% of dabigatran etexilate mesylate, 3.33% of Soluplus®, 16.7% of Kolliphor® P407 and 66.7% of sugar spheres.

Wherein, a method for preparing the neutral-core pellet may be conventional in the art, for example, all the components of the pharmaceutical composition are dissolved in an organic solvent, and the obtained mixture is sprayed to the neutral core. Preferably, the method for preparing the neutral-core pellet comprises the following steps: dissolving all the components of the pharmaceutical composition in an ethanol aqueous solution, and spraying the obtained solution to the neutral cores, wherein a mass fraction of ethanol in the ethanol aqueous solution is 90% to 95%.

When the pharmaceutical composition exists in the form of an acid-core pellet, the acid-core pellet comprises an acid core, an isolation layer and a drug layer, the isolation layer wraps the surface of the acid core, and the drug layer wraps the surface of the isolation layer; and the isolation layer comprises Soluplus® and Kolliphor® P407.

Wherein, the acid core may be an acid core conventionally used in the art, such as tartaric acid core.

Wherein, a mass percentage of the acid cores in the acid-core pellets may be conventional in the art, and is preferably 17% to 36%.

Wherein, the isolation layer wraps the surface of the acid core, that is, all components in the isolation layer wrap the surface of the acid core in a uniformly-mixed state. A mass percentage of Soluplus® in the isolation layers in the acid-core pellet is preferably 9% to 13%. A mass percentage of Kolliphor® P407 in the isolation layer in the acid-core pellet is preferably 4% to 6%.

Wherein, the drug layer wraps the surface of the isolation layer, that is, all components in the drug layer wrap the surface of the isolation layer in a solid dispersion mode. Preferably, the drug layer comprises the active pharmaceutical ingredient, Soluplus® and Kolliphor® P407, a mass percentage of the active pharmaceutical ingredient in the drug layer in the acid-core pellet is 14% to 19%, a mass percentage of Soluplus® in the drug layer in the acid-core pellet is 12% to 17%, and a mass percentage of Kolliphor® P407 in the drug layer in the acid-core pellet is 22% to 29%.

Wherein, preferably, the mass percentage of the acid core in the acid-core pellet is 17% to 36%; the mass percentage of Soluplus® in the isolation layer in the acid-core pellets is 9% to 13%, and the mass percentage of Kolliphor® P407 in the isolation layer in the acid-core pellet is 4% to 6%; and the drug layer comprises the active pharmaceutical ingredient, Soluplus® and Kolliphor® P407, the mass percentage of the active pharmaceutical ingredient in the drug layer in the acid-core pellet is 14% to 19%, the mass percentage of Soluplus® in the drug layer in the acid-core pellet is 12% to 17%, and the mass percentage of Kolliphor® P407 in the drug layer in the acid-core pellet is 22% to 29%.

In a preferred embodiment of the present disclosure, the mass percentage of the acid core in the acid-core pellet is 35.7%; the mass percentage of Soluplus® in the isolation layer in the acid-core pellet is 9.6%, and the mass percentage of Kolliphor® P407 in the isolation layer in the acid-core pellet is 4.7%; and the drug layer comprises the active pharmaceutical ingredient, Soluplus® and Kolliphor® P407, the mass percentage of the active pharmaceutical ingredient in the drug layer in the acid-core pellet is 14.4%, the mass percentage of Soluplus® in the drug layer in the acid-core pellet is 12.9%, and the mass percentage of Kolliphor® P407 in the drug layer in the acid-core pellet is 22.6%.

When the pharmaceutical composition exists in the form of granules, a method for preparing the granules may be a granulation method conventional in the art, such as wet granulation (a solvent adopted in the wet granulation is preferably isopropanol), roller-compaction granulation, fluidized bed granulation or hot melting granulation. In the granules prepared through the granulation method, the active pharmaceutical ingredient and the other components in the pharmaceutical composition are physically mixed to form a uniformly-mixed system. Certainly, in order to enable the pharmaceutical composition to exist in the form of the granules, a conventional granulation method in the art may further be adopted to enable the active pharmaceutical ingredient and the other components in the pharmaceutical composition to jointly form a solid dispersion.

Wherein, preferably, the method for preparing the granules is the hot melting granulation, and when the pharmaceutical composition does not contain a lubricant, the method for preparing the granules preferably comprises the following steps: mixing Soluplus® powder and the other components in the pharmaceutical composition to form uniform granules. Preferably, the grain size of the Soluplus® powder is less than 120 meshes. Preferably, a mixing temperature is 70 to 75° C.

Wherein, preferably, the method for preparing the granules is the hot melting granulation, and when the pharmaceutical composition contains a lubricant, the method for preparing the granules preferably comprises the following steps: mixing Soluplus® powder obtained after Soluplus® in the pharmaceutical composition is milled and the other components in the pharmaceutical composition to form uniform granules, and then mixing the granules with the lubricant. Preferably, the grain size of the Soluplus® powder is less than 120 meshes. Preferably, a mixing temperature is 70 to 75° C.

When the hot melting granulation described above is adopted, preferably, the pharmaceutical composition comprises the components of following mass fraction: 16% to 45% of the active pharmaceutical ingredient, 9% to 40% of the amphiphilic polymer, 19% to 23% of the hydrophilic polymer, 9% to 20% of the diluent, 4% to 23% of the disintegrating agent and 0.4% to 0.5% of the lubricant. The active pharmaceutical ingredient is preferably dabigatran etexilate mesylate. The amphiphilic polymer is preferably Soluplus®. The hydrophilic polymer is preferably Kolliphor® P407 and/or Kolliphor® P188. The diluent is preferably lactose monohydrate and/or mannitol. The disintegrating agent is preferably croscarmellose sodium and/or low-substituted hydroxypropyl cellulose. The lubricant is preferably magnesium stearate.

As described above, the pharmaceutical composition may exist in the forms of powder, pellets, granules, capsules or tablets. Preferably, the active pharmaceutical ingredient and the other components in the pharmaceutical composition jointly form a solid dispersion. More preferably, the amphiphilic polymer in the pharmaceutical composition exists in two existence forms simultaneously, the first existence form is that the amphiphilic polymer and the active pharmaceutical ingredient form a solid dispersion, and the second existence form is that the amphiphilic polymer exists in a form of solid granules.

Wherein, preferably, a mass fraction of the amphiphilic polymer existing in the first existence form accounts for 10% to 100% of total mass of the amphiphilic polymer, but not 100%.

Wherein, the solid granules may be powder of the amphiphilic polymer, and may further include the components of following mass fraction: 40% to 100% of the amphiphilic polymer, 0% to 55% of the diluent, 0% to 55% of the hydrophilic polymer, 0% to 20% of the disintegrating agent, 0% to 5% of the antistatic agent and 0% to 2% of the lubricant. Specifically, the solid granule comprises the components of following mass fraction: 40% to 100% of Soluplus®, 0% to 55% of Kolliphor® P407 and/or Kolliphor® P188, 0% to 55% of lactose monohydrate and/or mannitol, 0% to 20% of croscarmellose sodium, 0% to 5% of silica and 0% to 2% of magnesium stearate.

Preferably, the solid granule comprises the components of following mass fraction: 40% to 58% of the amphiphilic polymer, 0% to 55% of the diluent, 0% to 55% of the hydrophilic polymer, 5% to 20% of the disintegrating agent, 0% to 5% of the antistatic agent and 0% to 2% of the lubricant.

More preferably, the solid granule comprises the components of following mass fraction: 40% to 50% of Soluplus®, 0% to 55% of lactose, 5% to 20% of croscarmellose sodium, 0% to 5% of silica and 0% to 2% of magnesium stearate.

More preferably, the solid granule comprises the components of following mass fraction: 40% to 50% of Soluplus®, 0% to 55% of Kolliphor® P407, 5% to 20% of croscarmellose sodium, 0% to 5% of silica and 0% to 2% of magnesium stearate.

More preferably, the solid granule comprises the components of following mass fraction: 41% to 58% of Soluplus®, 3% to 33% of mannitol, 13% to 26% of Kolliphor® P407, 5% to 20% of croscarmellose sodium, 0% to 5% of silica and 0% to 2% of magnesium stearate.

More preferably, the solid granule comprises the components of following mass fraction: 41.9% to 50% of the amphiphilic polymer, 24.7% to 51.9% of the diluent, 19.8% to 51.9% of the hydrophilic polymer, 5.0% to 5.25% of the disintegrating agent, 0.1% to 1% of the lubricant and 0.1% to 1% of the antistatic agent. The active pharmaceutical ingredient is preferably dabigatran etexilate mesylate. The amphiphilic polymer is preferably Soluplus®. The hydrophilic polymer is preferably Kolliphor® P407 and/or Kolliphor® P188. The diluent is preferably lactose monohydrate and/or mannitol. The disintegrating agent is preferably croscarmellose sodium and/or the low-substituted hydroxypropyl cellulose. The lubricant is preferably magnesium stearate. The antistatic agent is preferably silica.

Wherein, preferably, a mass percentage of the mass of the solid granule is 9% to 35% of the total mass of the pharmaceutical composition.

In a preferred embodiment of the present disclosure, the solid granule is composed of the components of following mass fraction: 41.88% of Soluplus®, 51.87% of lactose monohydrate, 5.25% of croscarmellose sodium, 0.5% of magnesium stearate and 0.5% of silica.

In a preferred embodiment of the present disclosure, the solid granule is composed of the components of following mass fraction: 41.88% of Soluplus®, 51.87% of Kolliphor® P407, 5.25% of croscarmellose sodium, 0.5% of magnesium stearate and 0.5% of silica.

In a preferred embodiment of the present disclosure, the solid granule is composed of the components of following mass fraction: 49.5% of Soluplus®, 24.7% of mannitol, 19.8% of Kolliphor® P407, 5.0% of croscarmellose sodium, 0.5% of magnesium stearate and 0.5% of silica.

Wherein, when the solid granule includes accessories (the accessories here are other components except Soluplus®), a method for preparing the solid granule may be a granulation method conventional in the art, such as wet granulation (a solvent adopted in the wet granulation is preferably isopropanol), rolling granulation, fluidized bed granulation or hot melting granulation.

Wherein, preferably, the method for preparing the solid granule is the hot melting granulation, and when the solid granule does not contain a lubricant, the method for preparing the solid granule preferably comprises the following steps: mixing Soluplus® powder and the other components in raw materials of the solid granule to form uniform granule. Preferably, the grain size of the Soluplus® powder is less than 120 meshes, and a mixing temperature is 70 to 75° C.

Wherein, preferably, the method for preparing the solid granule is the hot melting granulation, and when the solid granule contains a lubricant, the method for preparing the solid granule preferably comprises the following steps: mixing Soluplus® powder and the other components in raw materials of the solid granule to form uniform granule, and then mixing the uniform granules with the lubricant. Preferably, the grain size of the Soluplus® powder is less than 120 meshes, and a mixing temperature is 70 to 75° C.

When the pharmaceutical composition exists in the form of a capsule, the capsule shell of the capsule contains one or more selected from the group consisting of the powder, the pellet and the granule described above. Preferably, the capsule shell of the capsule contains the powder, the pellet or the granule, wherein the capsule shell may be a capsule shell conventionally used in the art.

When the pharmaceutical composition exists in the form of a tablet, the tablet contains one or more selected from the group consisting of the powder, the pellet and the granule described above. Preferably, the tablet contains the powder, the pellet or the granule.

In the present disclosure, the pharmaceutical composition may be administered orally to patients in a form of a solution or a suspension, and the solution or the suspension is prepared after dispersing one or more selected from the group consisting of the powder, the pellet and the granule described above. Preferably, the solution or the suspension is prepared after dispersing the pellet described above, wherein a volume of water in the solution or the suspension may be, for example. 10 to 50 mL.

In the present disclosure, preferably, the pharmaceutical composition is administered orally to patients in a form of a capsule or a tablet, and the content of the active pharmaceutical ingredient in the capsule or the tablet must generate the maximum dabigatran plasma concentration of 40 to 200 ng/mL. More preferably, the content of the active pharmaceutical ingredient in the capsule or the tablet must generate the maximum dabigatran plasma concentration of 70 to 175 ng/mL. Further more preferably, the content of the active pharmaceutical ingredient in the capsule or the tablet must generate the maximum dabigatran plasma concentration of 100 to 150 ng/mL. The maximum dabigatran plasma concentration may be determined based on research of single-dosage fasting of healthy volunteers or patients.

The present disclosure further provides a method for preparing the pharmaceutical composition.

When the pharmaceutical composition does not contain the neutral core and exists in a form of powder, a method for preparing the powder preferably comprises the following steps: dissolving all components of the pharmaceutical composition in an ethanol aqueous solution, and carrying out spray-drying.

Wherein, preferably, the mass fraction of ethanol in the ethanol aqueous solution is 90% to 95%.

When the pharmaceutical composition does not contain the neutral core and exists in a form of a granule, the method for preparing the granule comprises the following steps: with isopropanol as a granulation solvent, carrying out wet granulation on a mixture of all the components of the pharmaceutical composition to obtain wet granule; and then performing drying after the wet granule is sieved by a 20-mesh sieve.

When the pharmaceutical composition does not contain the neutral core and exists in the form of a granule, a hot melting granulation is more preferably adopted for the pharmaceutical composition, and the hot melting granulation method comprises the following steps:

When the pharmaceutical composition does not contain a lubricant, the method for preparing the granule comprises the following steps: mixing Soluplus® powder with the other components in the pharmaceutical composition to form uniform granule. Preferably, the grain size of the Soluplus® powder is less than 120 meshes. Preferably, a mixing temperature is 70 to 75° C.

When the pharmaceutical composition contains a lubricant, the method for preparing the granule comprises the following steps: mixing Soluplus® powder with the other components in the pharmaceutical composition to form uniform granule, and then mixing the granule with the lubricant. Preferably, the grain size of the Soluplus® powder is less than 120 meshes. Preferably, a mixing temperature is 70 to 75° C.

When the pharmaceutical composition contains a neutral core and exists in a form of a neutral-core pellet, the method for preparing the neutral-core pellet comprises the following steps: spraying a coating solution to the neutral core, wherein the coating solution is formed by dissolving other components in the pharmaceutical composition except the neutral core in an organic solvent.

Wherein, the neutral core is pre-dried neutral core, and moisture content of the pre-dried neutral core is preferably lower than 1.0 wt %.

Wherein, the organic solvent is preferably an ethanol solution. The mass fraction of the ethanol in the ethanol aqueous solution is preferably 90% to 95%.

Wherein, a mass percentage of the pharmaceutical composition in the coating solution is preferably 20% to 24%.

Wherein, in the spraying process, an inlet temperature of air is preferably 45 to 60° C.

Wherein, in the spraying process, a temperature of the granule is preferably 30 to 50° C.

Wherein, after spraying is finished, the granule is preferably dried till moisture content is lower than 1.0 wt %.

When the pharmaceutical composition contains an acid core and exists in a form of an acid-core pellet, the method for preparing the acid-core pellet preferably comprises the following steps:

(1) spraying a coating solution to the acid core to obtain acid granule, wherein the coating solution is formed by dissolving all the components of the isolation layer in an organic solvent; and (2) spraying a coating solution to the acid granule, wherein the coating solution is formed by dissolving all the components of the drug layer in an organic solvent.

In step (1), the acid core is pre-dried acid core, and moisture content of the pre-dried acid core is preferably lower than 1.0 wt %.

In step (1), the organic solvent is preferably an ethanol solution. The mass fraction of ethanol in the ethanol aqueous solution is preferably 90% to 95%.

In step (1), a mass percentage of the pharmaceutical composition in the coating solution is preferably 20% to 26%.

In step (1), in the spraying process, an inlet temperature of air is preferably 45 to 60° C.

In step (1), in the spraying process, a temperature of the acid granule is preferably 30 to 32° C.

In step (1), after spraying is finished, the acid granule is preferably dried till moisture content is lower than 1.0 wt %.

In step (2), the organic solvent is preferably an ethanol solution. The mass fraction of ethanol in the ethanol solution is preferably 90% to 95%.

In step (2), a mass percentage of the pharmaceutical composition in the coating solution is preferably 20% to 24%.

In step (2), in the spraying process, an inlet temperature of air is preferably 45 to 60° C.

In step (2), in the spraying process, a temperature of the acid-core pellet is preferably 30 to 32° C.

In step (2), after spraying is finished, the acid-core pellet is preferably dried till moisture content is lower than 1.0 wt %.

The present disclosure further provides a use of the pharmaceutical composition described above in manufacturing a medicament for treating stroke caused by non-cardiac valve issues in atrial fibrillation patients and/or thrombus caused by the non-cardiac valve issues in the atrial fibrillation patients.

The present disclosure further provides a use of the pharmaceutical composition described above in manufacturing a medicament for treating deep venous thrombosis and/or pulmonary embolism.

The solid dosage forms prepared by the pharmaceutical composition of the present disclosure should be stable during manufacturing and storage. During manufacturing, normal storage (25° C./60% RH) and accelerated storage (40° C./75% RH), increase of drug impurities should be prevented. When the solid dosage form is stored for at least six months, preferably at least one year and most preferably at least two years, under about 25° C. and about 60% relative humidity, or, at least three months, most preferably six months, under about 40° C. and about 75% relative humidity, impurities in the solid dosage form should not exceed the following mass indexes: an impurity 1≤0.2%, an impurity 2≤0.5%, an impurity 3≤0.5%, an impurity 4≤0.1%, an impurity 5≤0.6%, an impurity 6≤0.5%, an impurity 7≤0.1%, an impurity 8≤0.25%, an impurity 9≤0.15%, an impurity 10≤2.5%, a single unknown impurity≤0.2%, and the total impurities≤3.6%. When the solid dosage form of the present disclosure is stored in a container (such as a plastic bottle) with a drying agent for six months under about 40° C. and about 75% relative humidity conditions, levels of all degradation products and/or impurities of the solid dosage form should meet requirements of the above mass indexes. Individual and total degradation products and/or impurities are based on the total amount of DEM in the solid dosage form. The types and content of the impurities may be determined through methods commonly used in the pharmaceutical art, such as high performance liquid chromatography (HPLC).

In the present disclosure, a manufacturer of the Eudragit® L100 is Evonik Special Chemistry (Shanghai) Co., Ltd; a manufacturer of the Klucel™ EF is Ashland; a manufacturer of Kollicoat® IR (polyethylene glycol-polyvinyl alcohol graft copolymer) is BASF; a manufacturer of the Kollidon® VA64 is BASF; a manufacturer of the Kolliphor® P188 is BASF; a manufacturer of the Kolliphor® P407 is BASF; a manufacturer of the HPMC E5 is DOW; a manufacturer of the HPMC VLV is DOW; a manufacturer of HPMCP® HP55 (Cellulose, hydrogen 1,2-benzenedicarboxylate, 2-hydroxypropyl methyl ether) is Samsung Precision Chemistry Company of the South Korea; a manufacturer of HPMCAS MG (Hypromellose acetate succinate) is Shin/Etsu; a manufacturer of the PVP K12 is Ashland; a manufacturer of PVP K30 (polyvinylpyrrolidone) is Ashland; a manufacturer of the Soluplus® is BASF; a manufacturer of the croscarmellose sodium is FMC; and a manufacturer of the low-substituted hydroxypropyl cellulose is Shin/Etsu.

In the present disclosure, the adopted "include/comprise . . . " may further be expressed as "be composed of . . . ".

For example, the solid granule comprises the components of following mass fraction: 41% to 58% of Soluplus®, 3% to 33% of mannitol, 13% to 26% of Kolliphor® P407, 5% to 20% of croscarmellose sodium, 0% to 5% of silica and 0% to 2% of magnesium stearate.

The above-mentioned expression may further be expressed as: the solid granule is composed of the components of following mass fraction: 41% to 58% of Soluplus®, 3% to 33% of mannitol, 13% to 26% of Kolliphor® P407, 5% to 20% of croscarmellose sodium, 0% to 5% of silica and 0% to 2% of magnesium stearate.

On the basis of not violating common senses in the art, all the mentioned preferable conditions may be randomly combined, so preferred examples of the present disclosure are obtained.

The agents and raw materials adopted in the present disclosure are all commercially available.

The present disclosure has the positive effects that: the present disclosure provides the pharmaceutical composition containing dabigatran etexilate and the preparation method thereof. The dissolution profile of the pharmaceutical composition is nearly not affected by pH of gastrointestinal fluid, precipitation of the DEM in neutral-pH intestinal fluid may further be avoided, and thus the pharmaceutical composition may enhance oral absorption of the dabigatran etexilate or pharmaceutically acceptable salts thereof, improve bioavailability of the API, further lower absorption variability and meanwhile provide the more stable concentration of the dabigatran in plasma, thereby reducing adverse side effects and possibility of GIT hemorrhage. In addition, due to absorption enhancement, non-absorbed DEM in gastrointestinal tracts is remarkably reduced, thus further relieving GIT massive hemorrhage. When the API and the other components of the pharmaceutical composition jointly form the solid dispersion, all the DEM is pre-dissolved in a carrier (the carrier is other components except the API), saving the worry about dissolution of drugs. The carrier may quickly dissolve out under conditions of aqueous media and acid pH, so possibility of DEM recrystallization may be reduced and even eliminated, and therefore DEM absorption is further promoted.

DETAILED DESCRIPTION OF THE PREFERRED EMBODIMENT

Figure 1:
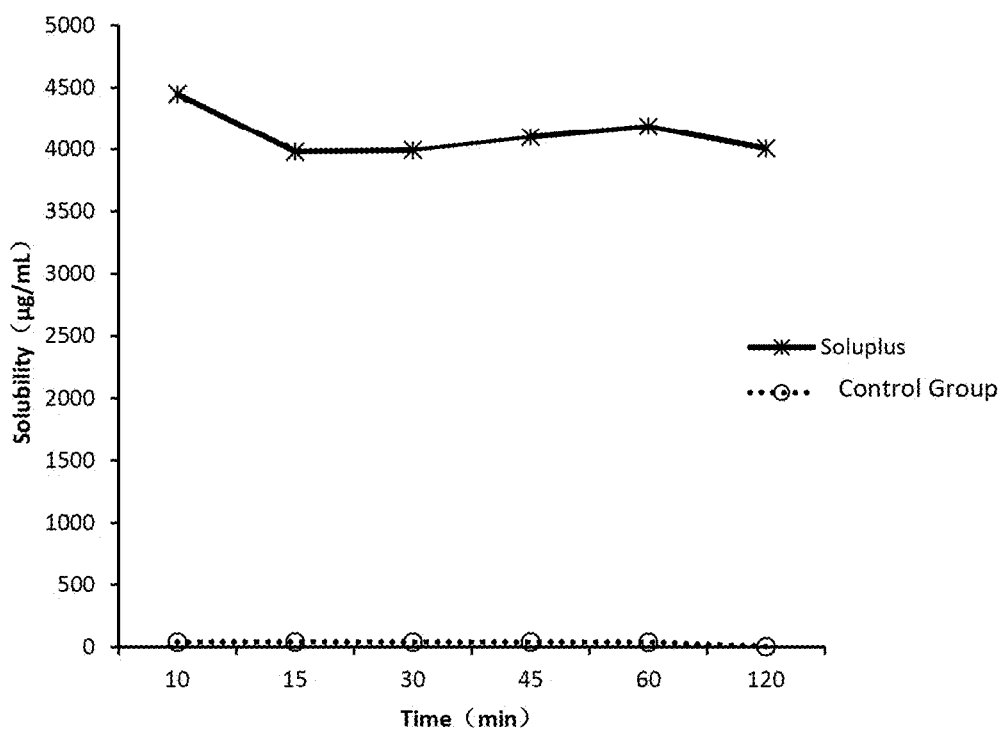
FIG. 1 shows a curve graph of solubility of APIs in a pharmaceutical composition with a polymer being Soluplus® and a pharmaceutical composition of a control group in Example 1 changing over time in a pH 6.8 and 25° C. phosphate buffer solution.

The present disclosure is further illustrated below through examples, but the present disclosure is not thus limited within the scope of the examples. Experiment methods in which specific conditions are not indicated in the following examples are in accordance with conventional methods and conditions, or selected according to product instructions.

In the following examples, a manufacturer of Eudragit® L100 is Evonik Special Chemistry (Shanghai) Co., Ltd; a manufacturer of Klucel™ EF is Ashland; a manufacturer of Kollicoat® IR is BASF; a manufacturer of Kollidon® VA64 is BASF; a manufacturer of Kolliphor® P188 is BASF; a manufacturer of Kolliphor® P407 is BASF; a manufacturer of HPMC E5 is DOW; a manufacturer of HPMC VLV is DOW; a manufacturer of HPMCP® HP55 is Samsung Precision Chemistry Company of the South Korea; a manufacturer of HPMCAS MG is Shin/Etsu; a manufacturer of PVP K12 is Ashland; a manufacturer of PVP K30 is Ashland; a manufacturer of Soluplus® is BASF; a manufacturer of croscarmellose sodium is FMC; and a manufacturer of low-substituted hydroxypropyl cellulose is Shin/Etsu.

In the following examples, in dissolution measuring experiments, an adopted pH 1.2 solution is a 0.085 N hydrochloric acid solution; an adopted pH 2.0 solution is a 0.01 N hydrochloric acid solution; an adopted pH 3.0 solution is a 0.001 N hydrochloric acid solution; an adopted pH 6.0 solution is a 0.000001 N hydrochloric acid solution; an adopted pH 4.5 solution is a 50 mM sodium acetate buffer solution; an adopted pH 6.8 solution is a 50 mM sodium phosphate buffer solution; and an adopted alkaline solution is a sodium hydroxide and sodium phosphate mixed solution.

Example 1

A screening experiment is performed in Example 1, the screening experiment aims to find polymers which may inhibit DEM precipitation under neutral pH, and the followings are polymers to be used for the screening experiment:

Eudragit® L100, Klucel™ EF, Kollicoat® IR, Kollidon® VA64, Kolliphor® P188, Kolliphor® P407, HPMC E5, HPMC VLV, HPMCP® HP55, HPMCAS MG, PVP K12, PVP K30 and Soluplus®.

The screening experiment includes the following steps.

1. A DEM stock solution is prepared with the drug concentration of 50 mg/mL in 0.1 N HCL.
2. 40 mg of the above polymer is placed in a 5 mL vial, and 3.6 mL of the pH 6.8 sodium phosphate buffer solution is added to dissolve the polymer to obtain a polymer solution.
3. 0.4 mL of the stock solution of step 1 is added into the polymer solution of step 2, and simultaneously 0.4 mL of the stock solution is added into a pH 6.8 phosphate buffer solution without polymers to serve as a control group.
4. The vial is shaken at 250 rpm under a room-temperature environment condition.
5. 0.4 mL of equivalent sample is taken at each time point of the $10^{th}$ minute, the $20^{th}$ minute, the $30^{th}$ minute, the $45^{th}$ minute, the $60^{th}$ minute and the $120^{th}$ minute.
6. The aliquots are centrifuged at 12,000 rpm for 5 minutes to obtain a supernatent.
7. The supernatent is diluted by 20 folds with a methanol and water mixed solution (the volume ratio of methanol to water is 1:1).
8. The DEM solution of step 7 is analyzed through HPLC.

Figure 2:
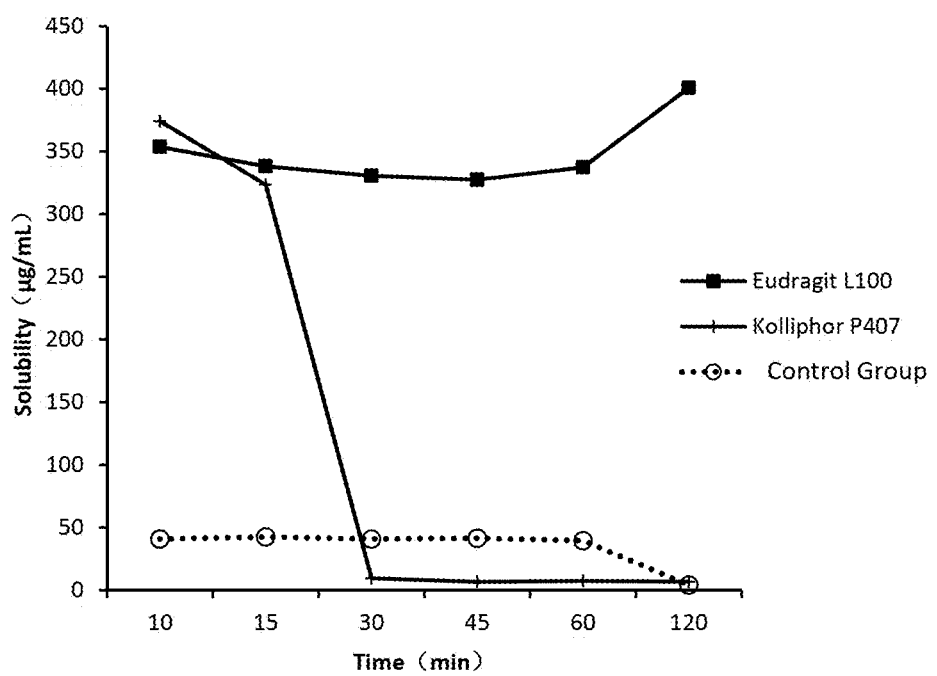
FIG. 2 shows a curve graph of solubility of APIs in pharmaceutical compositions with polymers being Eudragit® L100 and Kolliphor® P407 and the pharmaceutical composition of the control group in Example 1 changing over time in the pH 6.8 and 25° C. phosphate buffer solution.
Figure 3:
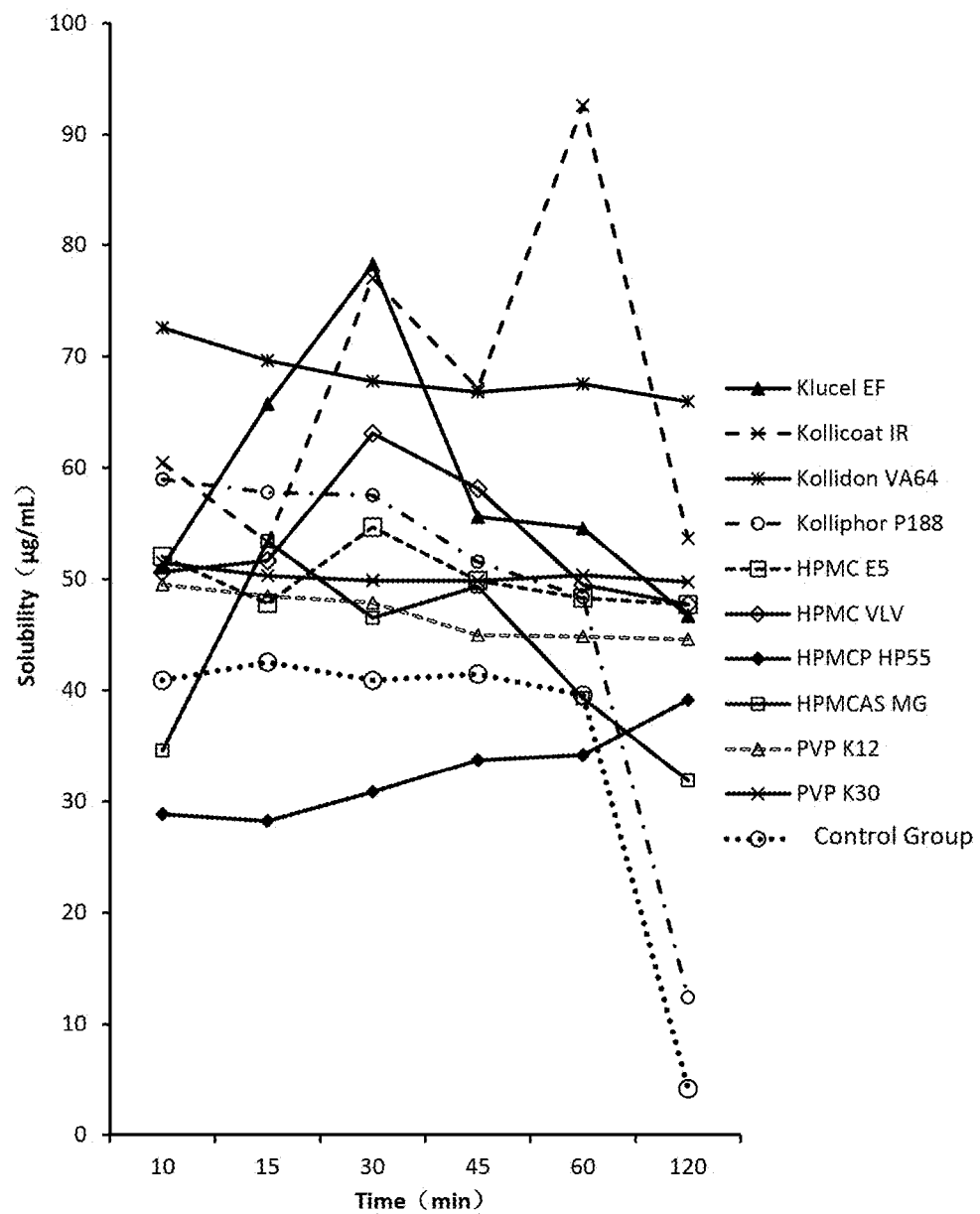
FIG. 3 shows a curve graph of solubility of APIs in pharmaceutical compositions with other polymers and the pharmaceutical composition of the control group in Example 1 changing over time in the pH 6.8 and 25° C. phosphate buffer solution.

Screening results are listed in Table 1, and the results are drawn in FIG. 1, FIG. 2 and FIG. 3. As can be seen from Table 1, FIG. 1, FIG. 2 and FIG. 3, as for the effect of inhibiting DEM precipitation under neutral pH 6.8, the Soluplus® is the optimal of all the screened polymers.

It should be further stated here that assuming that DEM is completely dissolved in the pH 6.8 phosphate buffer solution containing the polymers, the theoretical concentration of the DEM in the obtained DEM solution is about 5 mg/mL. It can thus be seen that after the DEM and the Soluplus® are matched, the DEM may be proximate to a complete dissolving state.

TABLE 1

Solubility of APIs in Example 1 Changing over Time

| | | | Time (min) | | | | | |
|---|---|---|---|---|---|---|---|---|
| | | / | 10 | 15 | 30 | 45 | 60 | 120 |
| Solubility (μg/mL) | 1 | Eudragit L100 | 353.56 | 338.07 | 330.5 | 327.35 | 337.25 | 400.65 |
| | 2 | Klucel EF | 51.07 | 65.74 | 78.24 | 55.59 | 54.55 | 46.73 |
| | 3 | Kollicoat IR | 60.45 | 53.3 | 77.02 | 67.12 | 92.58 | 53.63 |
| | 4 | Kollidon VA64 | 72.59 | 69.64 | 67.76 | 66.81 | 67.53 | 65.94 |
| | 5 | Kolliphor P188 | 58.97 | 57.81 | 57.56 | 51.56 | 48.4 | 12.4 |
| | 6 | Kolliphor P407 | 374.01 | 323.44 | 9.52 | 6.75 | 7.44 | 6.81 |
| | 7 | HPMC E5 | 52.04 | 47.85 | 54.66 | 49.88 | 48.32 | 47.73 |

TABLE 1-continued

Solubility of APIs in Example 1 Changing over Time

|   |   | Time (min) | | | | | |
|---|---|---|---|---|---|---|---|
| / | / | 10 | 15 | 30 | 45 | 60 | 120 |
| 8 | HPMC VLV | 50.65 | 51.66 | 63.09 | 58.15 | 49.5 | 47.76 |
| 9 | HPMCP HP55 | 28.86 | 28.25 | 30.87 | 33.74 | 34.21 | 39.15 |
| 10 | HPMCAS MG | 34.61 | 53.4 | 46.54 | 49.35 | 39.3 | 31.88 |
| 11 | PVP K12 | 49.53 | 48.49 | 47.91 | 44.99 | 44.86 | 44.6 |
| 12 | PVP K30 | 51.47 | 50.31 | 49.88 | 49.86 | 50.37 | 49.77 |
| 13 | Soluplus ® | 4448.9 | 3980.25 | 3992.25 | 4099.17 | 4186.57 | 4005.52 |
| Control Group | Control Group | 40.9 | 42.52 | 40.9 | 41.46 | 39.56 | 4.15 |

Example 2

A mini-dissolution experiment is performed in Example 2, the mini-dissolution experiment aims to evaluate dissolution behaviors of DEM solid dispersion films (SDF), the table below shows the composition of the SDFs to be evaluated in the mini-dissolution experiment, and all percentages are mass percentages.

| | Number | | | | | | | | | |
|---|---|---|---|---|---|---|---|---|---|---|
| | BN-009057-E | BN-009057-K | BN-009058-A | BN-009057-I | BN-009057-G | BN-009058-C | BN-009079-K | BN-009079-J | BN-009058-E | BN-009079-I |
| DEM | 20% | 20% | 20% | 20% | 20% | 20% | 20% | 20% | 100% (film) | 100% (powder) |
| Soluplus ® | 40% | 40% | 40% | 40% | 40% | 80% | / | / | / | / |
| PVP K12 | 40% | / | / | / | / | / | 80% | / | / | / |
| Kolliphor P188 | / | 40% | / | / | / | / | / | / | / | / |
| HPMC VLV | / | / | 40% | / | / | / | / | / | / | / |
| Klucel EF | / | / | / | 40% | / | / | / | / | / | / |
| HPMC E5 | / | / | / | / | 40% | / | / | / | / | / |
| Eudragit L100 | / | / | / | / | / | / | / | 80% | / | / |

In the example, a DEM SDF containing 3 mg of DEM is prepared in a 20 mL glass vials through a solvent evaporation method, then a dissolution medium is added, a dissolution experiment is performed at 37° C., and specific experiment steps are as follows:

1. ADEM stock solution with the drug concentration of 100 mg/mL is prepared in an ethanol solution with the volume fraction being 95%.
2. A polymer stock solution with the polymer concentration of 100 mg/mL is prepared in an ethanol solution with the volume fraction being 95%.
3. The stock solutions of step 1 and step 2 are added into 20 mL vials according to volumes shown in the following table, and full mixing is performed to obtain mixed solutions.

Wherein, BN-009058-E is a mixed solution obtained by adding the solution of step 1 into an ethanol solution with the volume fraction being 95% and fully mixing them, and BN-009079-J is not treated in this-step.

| | Number | | | | | | | | | | |
|---|---|---|---|---|---|---|---|---|---|---|---|
| | BN-009057-E | BN-009057-K | BN-009058-A | BN-009057-I | BN-009057-G | BN-009058-C | BN-009079-K | BN-009079-J | BN-009055-A | BN-009058-E | BN-009079-I |
| DEM | 200 µL | 200 µL | 200 µL | 200 µL | 200 µL | 200 µL | 200 µL | 200 µL | 200 µL | 200 µL | 3 mg |
| Soluplus ® | 400 µL | 400 µL | 400 µL | 400 µL | 400 µL | 800 µL | / | / | 400 µL | / | / |
| PVP K12 | 400 µL | / | / | / | / | / | 800 µL | / | / | / | / |
| Kolliphor P188 | / | 400 µL | / | / | / | / | / | / | / | / | / |
| HPMC VLV | / | / | 400 µL | / | / | / | / | / | / | / | / |
| Klucel EF | / | / | / | 400 µL | / | / | / | / | / | / | / |
| HPMC E5 | / | / | / | / | 400 µL | / | / | / | / | / | / |
| Kollidon VA64 | / | / | / | / | / | / | / | / | 400 µL | / | / |

-continued

| | Number | | | | | | | | | | |
|---|---|---|---|---|---|---|---|---|---|---|---|
| | BN-009057-E | BN-009057-K | BN-009058-A | BN-009057-I | BN-009057-G | BN-009058-C | BN-009079-K | BN-009079-J | BN-009055-A | BN-009058-E | BN-009079-I |
| Eudragit L100 | / | / | / | / | / | / | / | 800 μL | / | / | / |
| 95%EtOH | / | / | / | / | / | / | / | / | / | 800 μL | / |

4. 150 μL of each mixed solution or 3 mg of DEM powder is added into a 20 mL vial.

5. The mixed solutions and the 3 mg of DEM powder are dried for 30 minutes under environment conditions (flue), and then drying is performed in a vacuum drying box (drying conditions: 50° C., 10 mbar, 30 minutes) to ensure that films are rapidly and completely dried, so that the SDFs with the numbers in the above table are obtained.

6. 18 mL of the pH 6.8 sodium phosphate buffer solution is added into the vials of step 5, including the vial which only contains the DEM powder.

7. The vials are shaken at 200 rpm at 37° C.

8. Samples are taken at the $60^{th}$ minute.

9. The samples of step 8 are centrifuged at 12,000 rpm for 5 minutes to obtain a supernatent.

10. The supernatent is diluted by 20 times with a methanol and water mixed solution (the volume ratio of methanol to water is 1:1).

11. The DEM solution of step 10 is analyzed through HPLC.

Figure 4:
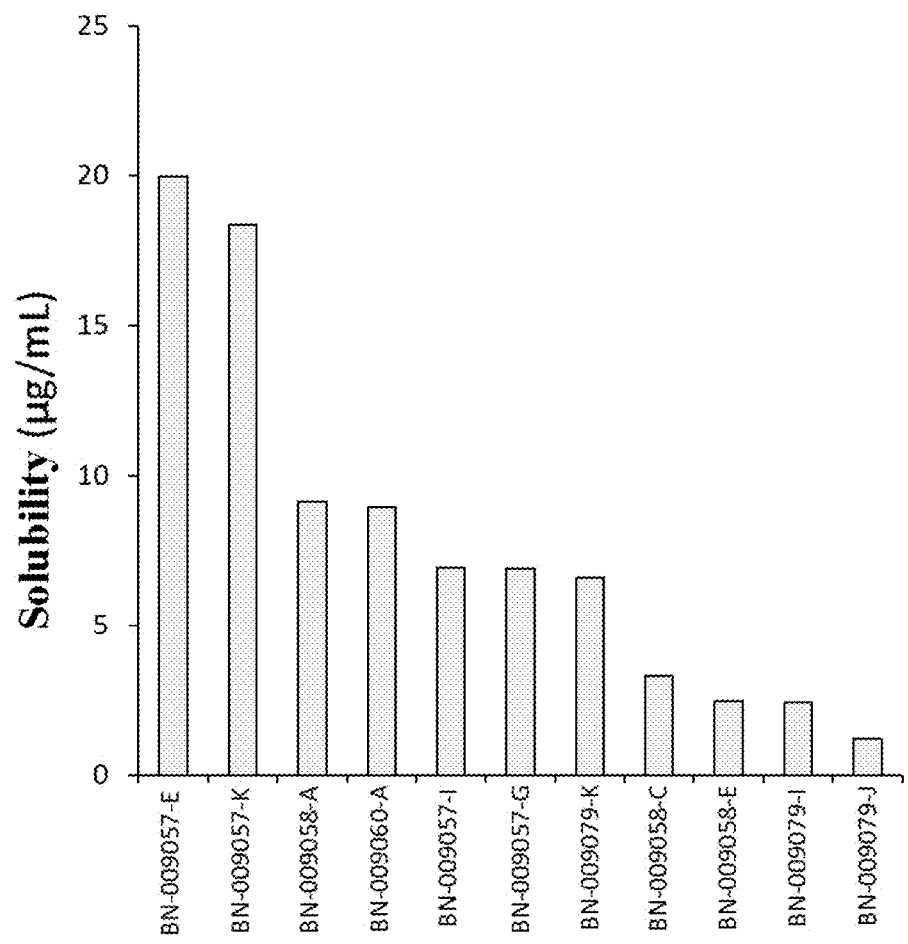
FIG. 4 shows solubility of APIs in all SDFs and a control group in Example 2 at the $60^{th}$ minute in a pH 6.8 and 37° C. phosphate buffer solution.

Screening results are listed in Table 2, and the results are drawn in FIG. 4. As can be seen from Table 2 and FIG. 4, combinations of Soluplus®/PVP K12 and Soluplus®/Kolliphor® P188 show the best results at the aspect of promoting dissolution under a neutral pH condition.

It should be further stated here that assuming that the DEM is completely dissolved in the pH 6.8 phosphate buffer solution containing the polymers, the theoretical concentration of the DEM in the obtained DEM solution is about 150 μg/mL.

TABLE 2

Solubility of APIs in All SDFs and Control Group at $60^{th}$ Minute in Example 2

| Number | Solubility (g/mL) |
|---|---|
| BN-009057-E (Soluplus ®:PVP K12 = 1:1) | 19.954 |
| BN-009057-K (Soluplus ®:Kolliphor P188 = 1:1) | 18.344 |
| BN-009058-A (Soluplus ®:HPMC VLV = 1:1) | 9.128 |
| BN-009060-A (Soluplus ®:Kollidon VA64 = 1:1) | 8.93 |
| BN-009057-I (Soluplus ®:Klucel EF = 1:1) | 6.912 |
| BN-009057-G (Soluplus ®:HPMC E5 = 1:1) | 6.882 |
| BN-009079-K (PVP K12) | 6.605 |
| BN-009058-C (Soluplus ®) | 3.318 |
| BN-009058-E (DEM Film control) | 2.473 |
| BN-009079-I (DEM Powder control) | 2.442 |
| BN-009079-J (Eudragit L100) | 1.243 |

Example 3

A mini-dissolution experiment is performed in Example 3, the mini-dissolution experiment aims to evaluate dissolution behaviors of DEM SDFs in the pH 4.5 sodium acetate buffer solution and the pH 6.8 sodium phosphate buffer solution, and specific experiment steps are the same as Example 2 and are as follows:

1. ADEM stock solution with the drug concentration of 100 mg/mL is prepared in a 95% ethanol solution.

2. A polymer stock solution with the polymer concentration of 100 mg/mL is prepared in a 95% ethanol solution.

3. The stock solutions of step 1 and step 2 are added into 20 mL vials according to volumes shown in the following table, and full mixing is performed to obtain mixed solutions.

Wherein, DEM F is a mixed solution obtained by adding the solution of step 1 into an ethanol solution with the volume fraction being 95% and fully mixing them, DEM P is not treated in this step, and DEM F and DEM P are control groups.

| | Number | | | | | | |
|---|---|---|---|---|---|---|---|
| | D/S (2:8) | D/K12 (2:8) | D/P407 (2:8) | D/S/K12 (2:4:4) | D/S/P407 (2:4:4) | DEM F | DEM P |
| DEM | 200 μL | 200 μL | 200 μL | 200 μL | 200 μL | 200 μL | 3 mg |
| Soluplus ® | 800 μL | / | / | 400 μL | 400 μL | / | / |
| PVP K12 | / | 800 μL | / | 400 μL | / | / | / |
| Kolliphor P407 | / | / | 800 μL | / | 400 μL | / | / |
| 95%EtOH | / | / | / | / | / | 800 μL | / |

4. 150 μL of each mixed solution or 3 mg of DEM powder is added into a 20 mL vial.

5. The mixed solutions and the 3 mg of DEM powder are dried for 30 minutes under environment conditions (flue), and then drying is performed in a vacuum drying cabinet (drying conditions: 50° C., 10 mbar, 30 minutes) to ensure that films are rapidly and completely dried, so that the SDFs with the numbers in the above table are obtained, wherein two films are prepared from each composition.

6. 18 mL of the pH 4.5 acetate buffer solution is added into one film of step 5, including the vial which only contains the DEM powder, and 18 mL of the pH 6.8 phosphate buffer solution is added into the other film of step 5, including the vial which only contains the DEM powder.

7. The vials are shaken at 200 rpm at 37° C.

8. Samples are taken at the 10$^{th}$ minute, the 20$^{th}$ minute, the 30$^{th}$ minute, the 45$^{th}$ minute, the 60$^{th}$ minute and the 120$^{th}$ minute.

9. The samples of step 8 are centrifuged at 12,000 rpm for 5 minutes to obtain a supernatent.

10. The supernatent is diluted by 20 times with a methanol and water mixed solution (the volume ratio of methanol to water is 1:1).

11. The DEM solution of step 10 is analyzed through HPLC.

Figure 5:
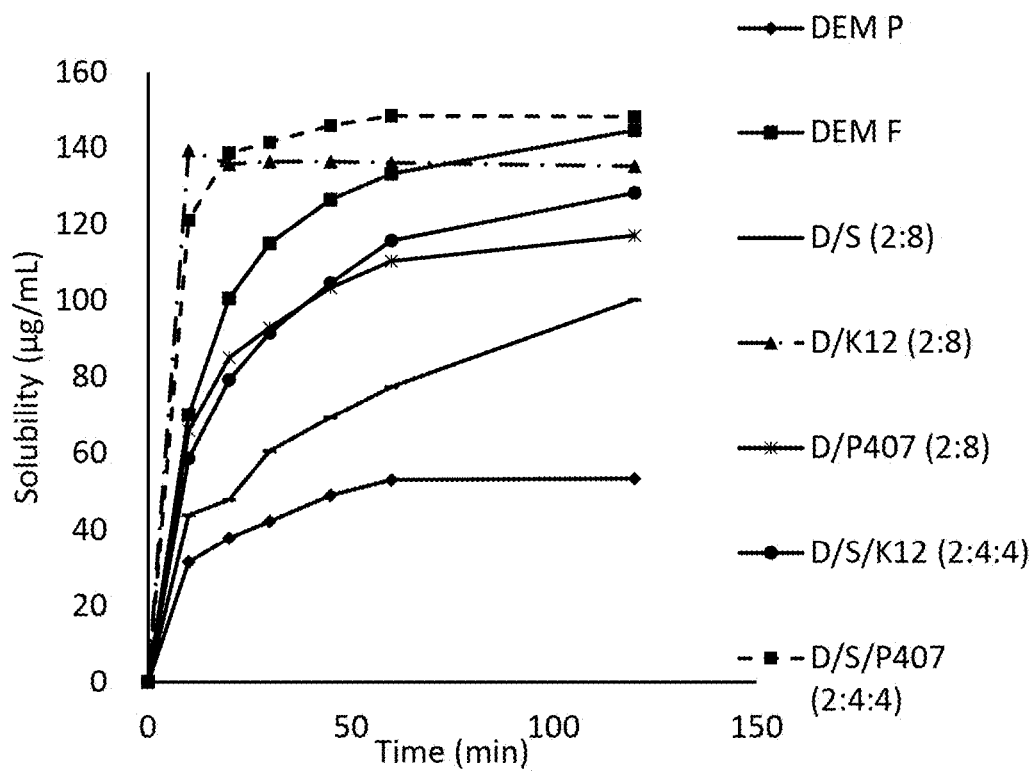
FIG. 5 shows a dissolution profile graph of APIs in all SDFs and control groups in Example 3 changing over time in a pH 4.5 and 37° C. acetate buffer solution.
Figure 6:
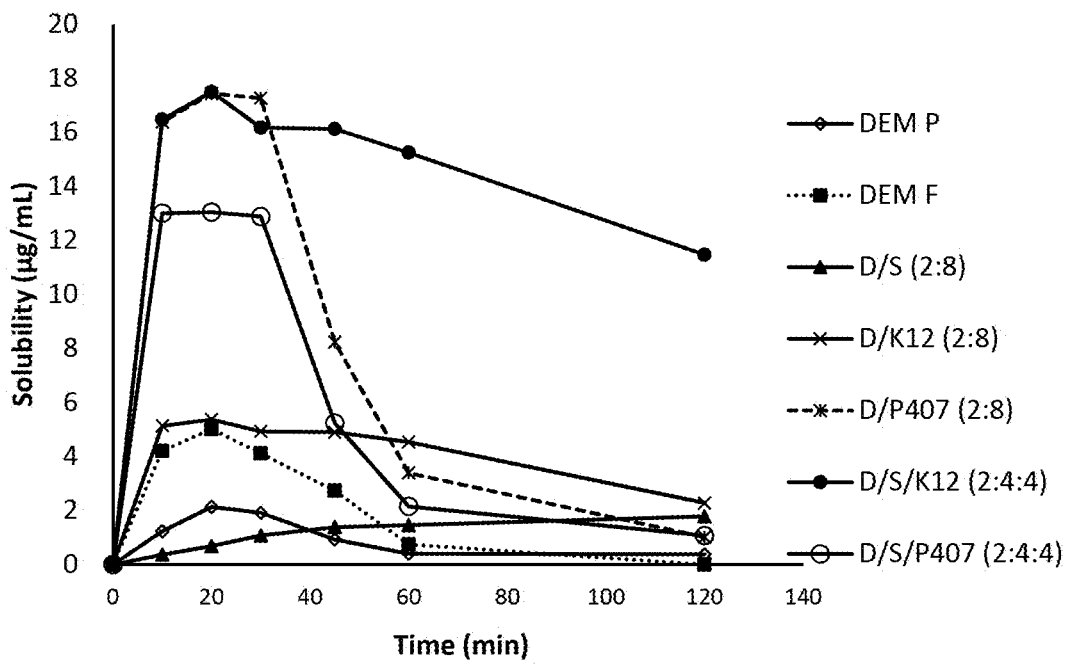
FIG. 6 shows a dissolution profile graph of the APIs in all the SDFs and the control groups in Example 3 changing over time in a pH 6.8 and 37° C. phosphate buffer solution.

Screening results are listed in Table 3 and Table 4, and the results are drawn in FIG. 5 and FIG. 6. As can be seen from Table 3, Table 4, FIG. 5 and FIG. 6, the SDFs of D/K12 (2:8) and D/S/P407 (2:4:4) show rapid dissolution under pH 4.5, and the SDFs of D/S/K12 (2:4:4), D/P407 (2:8) and D/S/P407 (2:4:4) show relatively good dissolution under pH 6.8.

It should be further stated here that assuming that the DEM is completely dissolved in the pH 6.8 phosphate buffer solution containing the polymers, the theoretical concentration of the DEM in the obtained DEM solution is about 150 μg/mL.

TABLE 3

Solubility of APIs in All SDFs and Control Groups in Example 3 Changing over Time (μg/mL)

| Time (min) | DEM P | DEM F | D/S (2:8) | D/K12 (2:8) | D/P407 (2:8) | D/S/K12 (2:4:4) | D/S/P407 (2:4:4) |
|---|---|---|---|---|---|---|---|
| 0 | 0 | 0 | 0 | 0.00 | 0.00 | 0.00 | 0.00 |
| 10 | 31.46 | 70.16 | 43.86 | 139.40 | 66.02 | 58.73 | 121.19 |

TABLE 3-continued

Solubility of APIs in All SDFs and Control Groups in Example 3 Changing over Time (μg/mL)

| Time (min) | DEM P | DEM F | D/S (2:8) | D/K12 (2:8) | D/P407 (2:8) | D/S/K12 (2:4:4) | D/S/P407 (2:4:4) |
|---|---|---|---|---|---|---|---|
| 20 | 37.81 | 100.66 | 47.90 | 135.81 | 85.07 | 79.30 | 138.69 |
| 30 | 42.20 | 115.10 | 60.67 | 136.42 | 93.00 | 91.54 | 141.55 |
| 45 | 49.05 | 126.52 | 69.41 | 136.49 | 103.44 | 104.69 | 145.90 |
| 60 | 53.10 | 133.33 | 77.50 | 136.15 | 110.42 | 115.80 | 148.44 |
| 120 | 53.44 | 144.65 | 100.29 | 135.25 | 117.14 | 128.32 | 148.20 |

TABLE 4

Solubility of APIs in All SDFs and Control Groups in Example 3 Changing over Time (μg/mL)

| Time (min) | DEM P | DEM F | D/S (2:8) | D/K12 (2:8) | D/P407 (2:8) | D/S/K12 (2:4:4) | D/S/P407 (2:4:4) |
|---|---|---|---|---|---|---|---|
| 0 | 0.00 | 0.00 | 0.00 | 0.00 | 0.00 | 0.00 | 0.00 |
| 10 | 1.23 | 4.21 | 0.37 | 5.13 | 16.38 | 16.47 | 13.00 |
| 20 | 2.13 | 5.01 | 0.69 | 5.37 | 17.43 | 17.49 | 13.04 |
| 30 | 1.92 | 4.11 | 1.08 | 4.93 | 17.25 | 16.17 | 12.88 |
| 45 | 0.93 | 2.73 | 1.38 | 4.90 | 8.23 | 16.12 | 5.24 |
| 60 | 0.40 | 0.75 | 1.46 | 4.53 | 3.39 | 15.25 | 2.15 |
| 120 | 0.38 | 0.00 | 1.78 | 2.28 | 1.01 | 11.47 | 1.08 |

Example 4

Example 4 aims to evaluate the influence of the amount of Soluplus® in and out of SDFs on solubility, especially the influence on drug precipitation in pH 6.8 neutral media.

The SDFs are prepared by repeating the steps in Example 2 in Example 4, and the difference is that SDF dissolution tests are performed through a two-stage dissolution method, wherein the first stage is performed in the pH 4.5 solution, and the second stage is performed in the pH 6.8 solution.

The following table shows compositions of the SDFs to be evaluated through the two-stage dissolution method.

| | | Mass of Components/mg Number | | | | | | |
|---|---|---|---|---|---|---|---|---|
| | | D/S/K12 (2/4/4) | D/K12 + S (2/4 + 4) | D/S/K12 (2/2/6) | D/K12 + S (2/6 + 2) | D/K12 + S (2/6 + 4) | D/S/P407 (2/3/5) | D/S/P407 + S (2/1/5 + 2) |
| Compositions of SDFs | DEM | 3.0 | 3.0 | 3.0 | 3.0 | 3.0 | 3.0 | 3.0 |
| | Soluplus ® | 6.0 | / | 3.0 | / | / | 4.5 | 1.5 |
| | PVP K12 | 6.0 | 6.0 | 9.0 | 9.0 | 9.0 | / | / |
| | Kolliphor P407 | / | / | / | / | / | 7.5 | 7.5 |
| Soluplus ® out of SDFs | | / | 6 | / | 3 | 6 | / | 3 |
| Total | | 15 | 15 | 15 | 15 | 18 | 15 | 15 |

Firstly, the SDFs with or without the Soluplus® out of the films are placed in 18 mL of the acetate buffer solution (pH 4.5 solution); at the $10^{th}$ minute, 0.4 mL of aliquots are taken, and then 2 mL of the alkaline solution is added to regulate pH to the target pH 6.8 (6.5 to 7.0); 10 minutes after pH regulation, aliquots (0.4 mL) are taken again; and the DEM concentration in each aliquot is analyzed.

Figure 7:
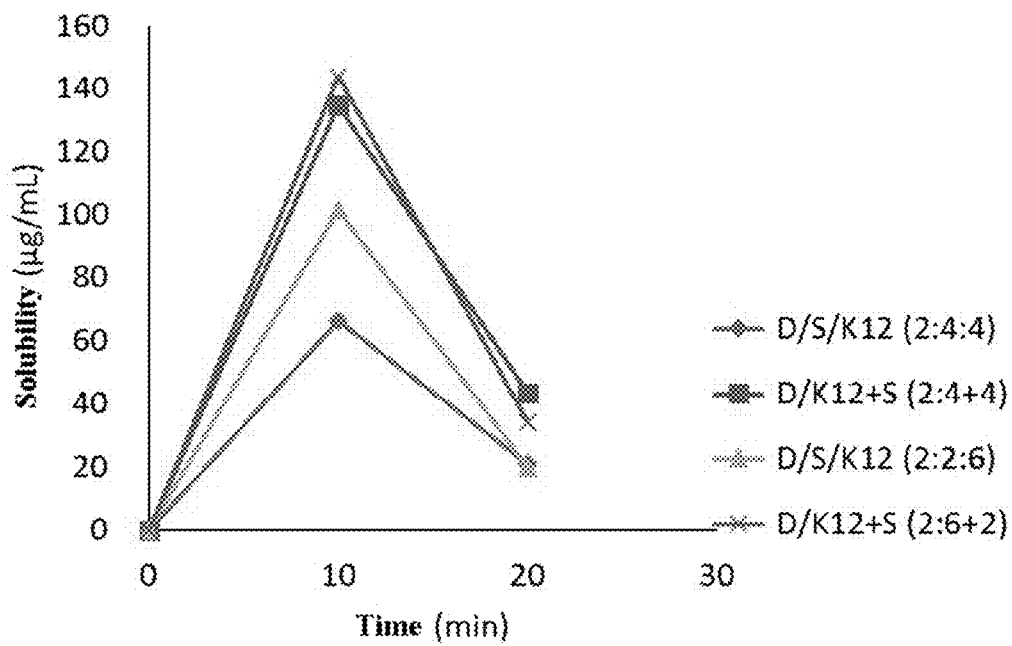
FIG. 7 shows a dissolution profile graph of APIs in all pharmaceutical compositions in Example 4 changing over time in a 37° C. pH 4.5 acetate buffer solution→pH 6.8 phosphate buffer solution two-stage dissolution experiment.
Figure 8:
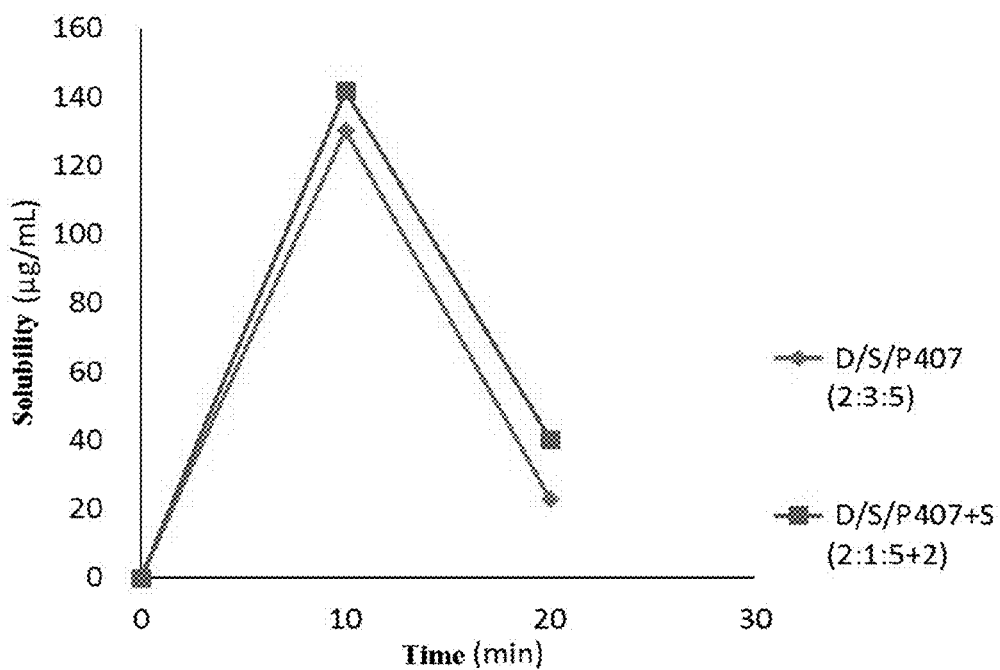
FIG. 8 shows a dissolution profile graph of the APIs in all the pharmaceutical compositions in Example 4 changing over time in the 37° C. pH 4.5 acetate buffer solution→pH 6.8 phosphate buffer solution two-stage dissolution experiment.
Figure 9:
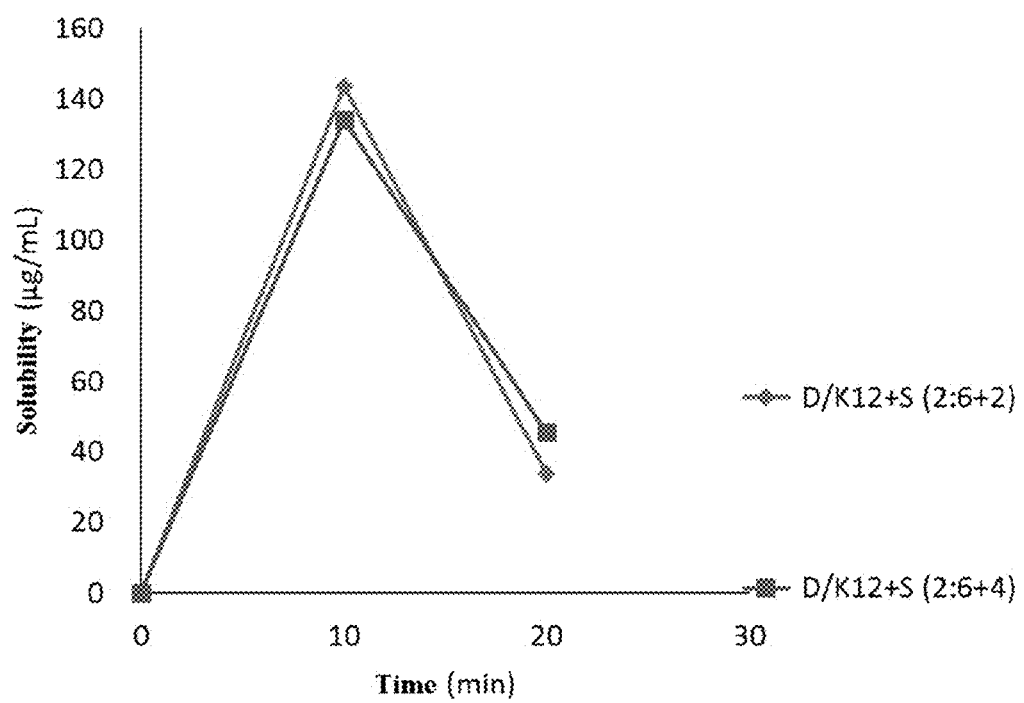
FIG. 9 shows a dissolution profiles graph of the APIs in all the pharmaceutical compositions in Example 4 changing over time in the 37° C. pH 4.5 acetate buffer solution→pH 6.8 phosphate buffer solution two-stage dissolution experiment.

Results are listed in Table 5, FIG. 7, FIG. 8 and FIG. 9, as can be seen from the results, dissolution is slowed down by the Soluplus® in the films, and therefore by replacing the Soluplus® in the films with the Soluplus® out of the films, not only is dissolution under acid pH (pH 4.5) accelerated, but also DEM separation under neutral pH (pH 6.8) is prevented.

TABLE 5

Solubility of APIs in All Pharmaceutical Compositions in Example 4 Changing over Time (μg/mL)

| Time (min) | D/S/K12 (2:4:4) | D/K12 + S (2:4 + 4) | D/S/K12 (2:2:6) | D/K12 + S (2:6 + 2) | D/K12 + S (2:6 + 4) | D/S/P407 (2:3:5) | D/S/P407 + S (2:1:5 + 2) |
|---|---|---|---|---|---|---|---|
| 10 (pH 4.5) | 66.23 | 134.59 | 101.19 | 143.42 | 134.11 | 130.02 | 141.52 |
| 20 (pH 6.8) | 20.87 | 43.18 | 19.87 | 34.02 | 45.41 | 22.68 | 40.16 |

Example 5

According to Table 6, pellets are prepared by spraying a solid dispersion composition to neutral cores, and the solid dispersion composition includes 30 wt % of DEM, 10 wt % of Soluplus®, and 60 wt % of Kolliphor® P407.

A specific preparation method is as follows:

Firstly, the solid dispersion composition is dissolved in 95 wt % ethanol to prepare a coating solution, wherein the coating solution contains 20 wt % of the solid dispersion composition; then, the neutral cores (300 to 500 μm) are pre-dried in an 80° C. convection oven until the moisture content of the neutral cores is lower than 1.0%; and afterwards, 300 g of the coating solution containing 60 g of the solid dispersion composition is sprayed to 40 g of the pre-dried neutral cores on a fluidized bed granulator with a Wurster insert under proper inlet air pressure and the 45 to 60° C. air inlet temperature, and in a spraying process, the spraying speed and atomization pressure are adjusted to enable the product temperature to be kept at 30 to 50° C. After the coating solution is used up, a product is dried in a fluidized bed until the moisture content is lower than 1.0%, and a target mass ratio of solid dispersion layers wrapping the neutral cores to the neutral cores is 1.5/1.0, so that the pellets in Example 5 are obtained.

TABLE 6

Compositions of Pellets F1

| / | Action | Components | Wt/% | Wt/mg |
|---|---|---|---|---|
| Solid dispersion composition | API | DEM | 18.0 | 173.0 |
| | Amphiphilic Polymer | Soluplus® | 6.0 | 57.7 |
| | Hydrophilic Polymer | Kolliphor P407 | 36.0 | 346.0 |
| | Neutral Cores | Sugar Spheres | 40.0 | 388.4 |

By using a USP basket type two-step method, at 100 rpm and 37° C., dissolution profiles of the pellets containing 173.0 mg of the DEM (equivalent to 150 mg of DEM freebase) are measured. In the first stage, the pellets are placed in 500 mL of acid media (the pH 2.0 solution), wherein the acid media contain Soluplus® with different mass (0 mg, 75 mg, 150 mg and 300 mg); and in the second stage ($45^{th}$ minute), 500 mL of the alkaline solution is added into the acid media to regulate pH to 6.8. 3 mL of aliquots are taken at the time points of the $10^{th}$ minute, the $45^{th}$ minute, the $55^{th}$ minute and the $90^{th}$ minute. The aliquots are centrifuged at 12,000 rpm for 5 minutes, and a supernate is diluted by 10 folds with a 1/1-volume-ratio methanol/water mixed solution so as to be used for HPLC analysis.

Figure 10:
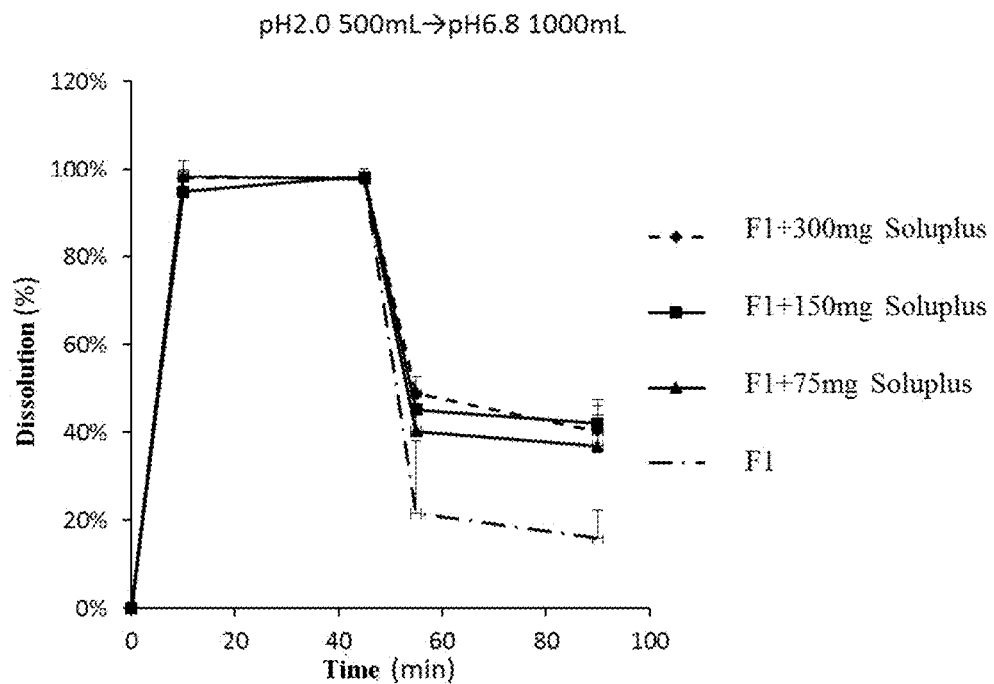
FIG. 10 denotes dissolution profile of pellets (F1) in Example 5 in solutions containing amphiphilic polymer of different concentrations, wherein an error bar represents a standard deviation of n=3.

Results are shown in Table 7 and FIG. 10, and as can be seen from FIG. 10, by adding 75 mg or more Soluplus® powder outside the pellets, the situation that more DEM is precipitated under neutral pH (pH 6.8) may be prevented.

TABLE 7

Dissolution of F1 in Media Containing Soluplus® of Different Concentrations in Example 5 Changing over Time

| | F1 + 300 mg Soluplus® | | F1 + 150 mg Soluplus® | | F1 + 75 mg Soluplus® | | F1 | |
|---|---|---|---|---|---|---|---|---|
| Time (min) | Dissolution % | SD % | Dissolution % | SD % | Dissolution % | SD % | Dissolution % | SD % |
| | pH 2.0 500 mL → pH 6.8 1000 mL | | | | | | | |
| 0 | 0.00 | 0.00 | 0.00 | 0.00 | 0.00 | 0.00 | 0.00 | 0.00 |
| 10 | 97.90 | 1.95 | 94.74 | 4.65 | 98.23 | 0.76 | 98.59 | 3.42 |
| 45 | 98.05 | 2.15 | 98.22 | 0.58 | 97.68 | 1.22 | 97.76 | 1.05 |
| 55 | 48.88 | 3.89 | 45.15 | 0.06 | 40.22 | 3.87 | 21.51 | 16.67 |
| 90 | 40.28 | 7.11 | 42.05 | 1.94 | 36.90 | 9.20 | 15.90 | 6.37 |

Example 6

Pellets F1 are prepared by repeating the steps in Example 5, and the difference from Example 5 is that externally-added Soluplus® in Example 6 is added in a form of powder.

Firstly, Soluplus® granules are milled and screened by an 80-mesh sieve to obtain 150 mg of Soluplus® powder (less than 80 meshes); then, the Soluplus® powder and 0.5 wt % (based on the mass of the Soluplus® powder, 150 mg) of silica are mixed to obtain solid granules; and finally, the pellets F1 are mixed with the solid granules to obtain pellets in Example 6.

Figure 11:
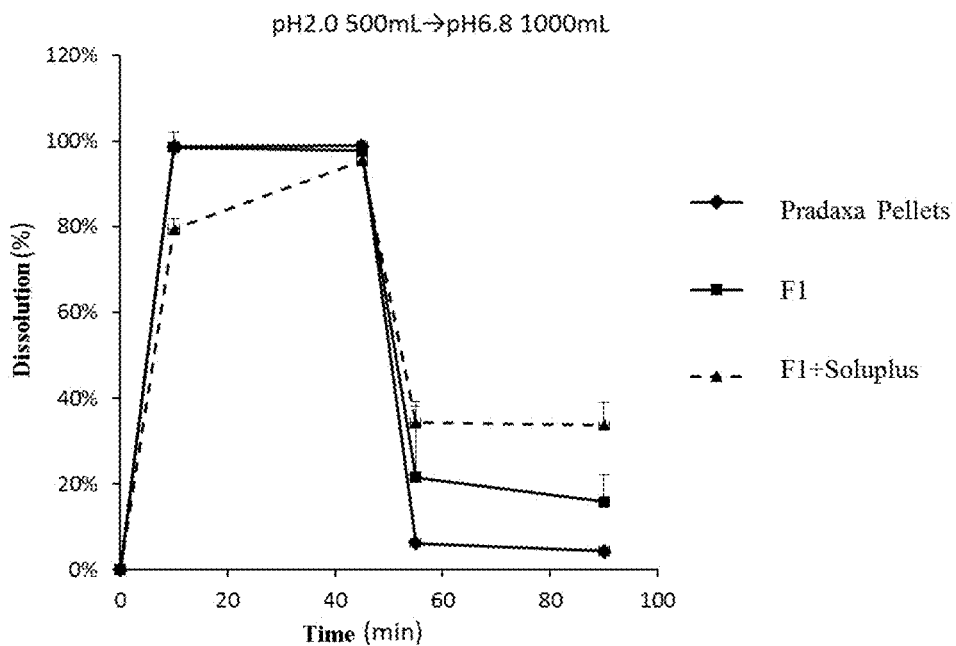
FIG. 11 denotes dissolution profiles of the pellets (F1) in Example 5, pellet+Soluplus® powder in Example 5 (namely pellets in Example 6) and Pradaxa Pellets, wherein the Pradaxa Pellets are capsule contents of Pradaxa Capsules, the Chinese trade name of the Pradaxa Capsules is Pradaxa, the strength is 150 mg, a manufacturer is Boehringer Ingelheim GmbH, and an error bar represents a standard deviation of n=3.

The test method which is the same as that in Example 5 is adopted to measure dissolution profile of the pellets F1, the pellets in Example 6 and Pradaxa Pellets (contents of Pradaxa Capsules), and results are shown in Table 8 and FIG. 11.

As can be seen from Table 8 and FIG. 11, compared with the Pradaxa Pellets, the pellets F1 may prevent DEM dissolved out from acid media from being precipitated under pH 6.8. However, the pellets containing the externally-added Soluplus® powder in Example 6 relieve dissolution of the DEM from the acid media.

TABLE 8

Dissolution of preparations in Example 6 Changing over Time

| Time (min) | Pradaxa Pelltes (150 mg) | | F1 (150 mg) | | F1 + Soluplus ® (150 mg) | |
|---|---|---|---|---|---|---|
| | Dissolution/% | SD % | Dissolution/% | SD % | Dissolution/% | SD % |
| | pH 2.0 500 mL → pH 6.8 1000 mL | | | | | |
| 0 | 0.00 | 0.00 | 0.00 | 0.00 | 0.00 | 0.00 |
| 10 | 98.66 | 0.84 | 98.59 | 3.42 | 79.39 | 2.44 |
| 45 | 98.85 | 1.13 | 97.76 | 1.05 | 95.45 | 3.61 |
| 55 | 6.26 | 0.55 | 21.51 | 16.67 | 34.34 | 5.00 |
| 90 | 4.39 | 0.08 | 15.90 | 6.37 | 33.78 | 5.35 |

Example 7

Pellets F2 are prepared by adopting the preparation method in Example 5.

Isopropyl alcohol (IPA) is used as a granulation solvent, and a mixture of all components of solid granules is subjected to wet granulation to obtain wet granules; and the wet granules are screened by a 20-mesh sieve and dried in a laminar flow hood under the ambient temperature to obtain solid granules.

TABLE 9

Compositions of Capsules F2-A and F2-B in Example 7

| Pellets F2 | | | |
|---|---|---|---|
| Action | Components | Wt % | Wt/capsule, mg |
| API | DEM | 24.0 | 57.7 |
| Amphiphilic Polymer | Soluplus ® | 6.0 | 14.4 |
| Hydrophilic Polymer | Kolliphor P407 | 30.0 | 72.1 |
| Neutral Cores | Sugar Spheres | 40.0 | 96.1 |
| / | Total | 100.0 | 240.3 |

| Solid Granules | | | | | |
|---|---|---|---|---|---|
| | | A | | B | |
| Action | Components | Wt % | Wt/capsule, mg | Wt % | Wt/capsule, mg |
| Amphiphilic Polymer | Soluplus ® | 41.88 | 75.0 | 41.88 | 75.0 |
| Diluting Agent | Lactose Monohydrate | 51.87 | 92.9 | / | / |
| Hydrophilic Polymer | Kolliphor P407 | / | / | 51.87 | 92.9 |
| Disintegrating Agent | croscarmellose sodium | 5.25 | 9.4 | 5.25 | 9.4 |
| Lubricant | Magnesium Stearate | 0.50 | 0.9 | 0.50 | 0.9 |
| Antistatic Agent | Silica | 0.50 | 0.9 | 0.50 | 0.9 |
| / | Total | 100.00 | 179.1 | 100.00 | 179.1 |

According to Table 9, gelatin capsules (#0) are filled with the pellets (240.3 mg) and the solid granules (179.1 mg) to obtain capsules F2-A and F2-B.

Figure 12:
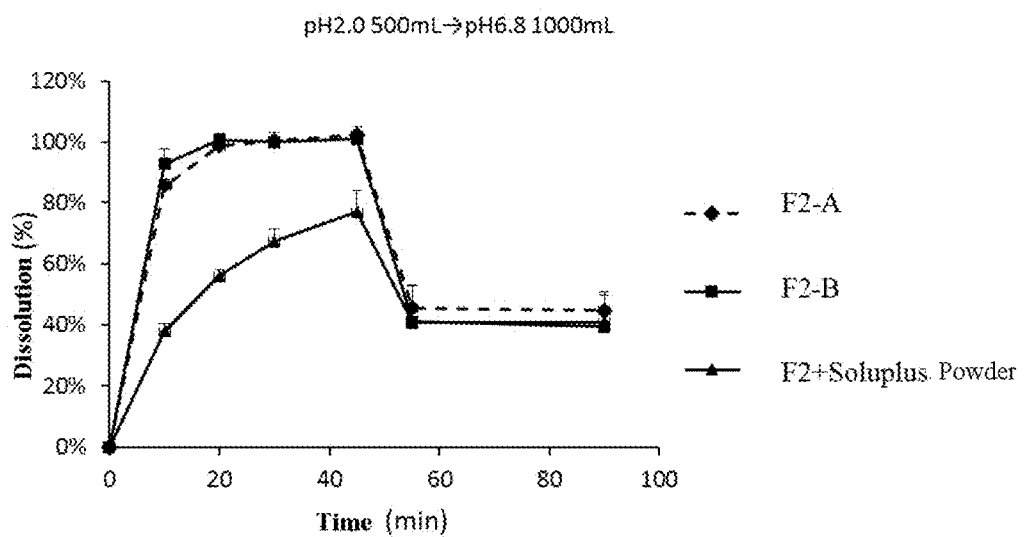
FIG. 12 denotes dissolution profiles of capsules (F2-A, F2-B and F2+Soluplus® powder) in Example 7 and the pellets in Example 6, wherein an error bar represents a standard deviation of n=3.

The test method which is the same as that in Example 5 is adopted to measure dissolution profile of the capsules F2-A and F72-B3, and results are shown in Table 10 and FIG. 12.

As can be seen from Table 10 and FIG. 12, compared with F2+Soluplus® powder (containing 75.0 mg of Soluplus® powder), the pellet preparations (F2-A and F2-B3) containing the solid granules in Example 7 show faster dissolution in the acid media.

TABLE 10

Dissolution of Preparations in Example 7 Changing over Time in Media containing Soluplus ® of Different Concentrations

| Time (min) | F2-A (50 mg) | | F2-B (50 mg) | | F2 + Soluplus ® Powder (50 mg) | |
|---|---|---|---|---|---|---|
| | Dissolution/% | SD % | Dissolution/% | SD % | Dissolution/% | SD % |
| | pH 2.0 500 mL → pH 6.8 1000 mL | | | | | |
| 0 | 0.00 | 0.00 | 0.00 | 0.00 | 0.00 | 0.00 |
| 10 | 85.65 | 2.21 | 92.99 | 4.73 | 37.93 | 2.68 |
| 20 | 98.91 | 3.74 | 100.92 | 0.97 | 55.98 | 1.95 |
| 30 | 100.38 | 2.73 | 100.03 | 1.43 | 67.31 | 4.12 |
| 45 | 102.40 | 2.85 | 101.15 | 1.40 | 76.81 | 7.02 |
| 55 | 45.57 | 7.07 | 41.13 | 12.00 | 40.74 | 3.30 |
| 90 | 44.79 | 5.93 | 39.45 | 10.44 | 40.92 | 3.06 |

Example 8

Granules F3 containing DEM are prepared by repeating the wet granulation steps in Example 7.

| Action | Components | Wt/% | Wt/capsule, mg |
|---|---|---|---|
| API | DEM | 17.0 | 57.7 |
| Amphiphilic Polymer | Soluplus ® | 39.2 | 132.9 |
| Diluting Agent | Lactose Monohydrate | 38.3 | 130.0 |
| Disintegrating Agent | croscarmellose sodium | 5.0 | 17.0 |
| Lubricant | Magnesium Stearate | 0.5 | 1.7 |
| / | Total | 100.0 | 339.3 |

According to the above table, gelatin capsules (#0) are filled with the granules (339.3 mg) containing the DEM.

Test Method:

Different from the test method in Example 5, considering change of pH values of stomachs, pH of the first stage is set as 1.2 or 2.0 or 3.0 (namely acid media adopted in the first stage are respectively: the pH 1.2 solution, the pH 2.0 solution and the pH 3.0 solution), and other aspects are the same as the test method in Example 5.

Figure 13:
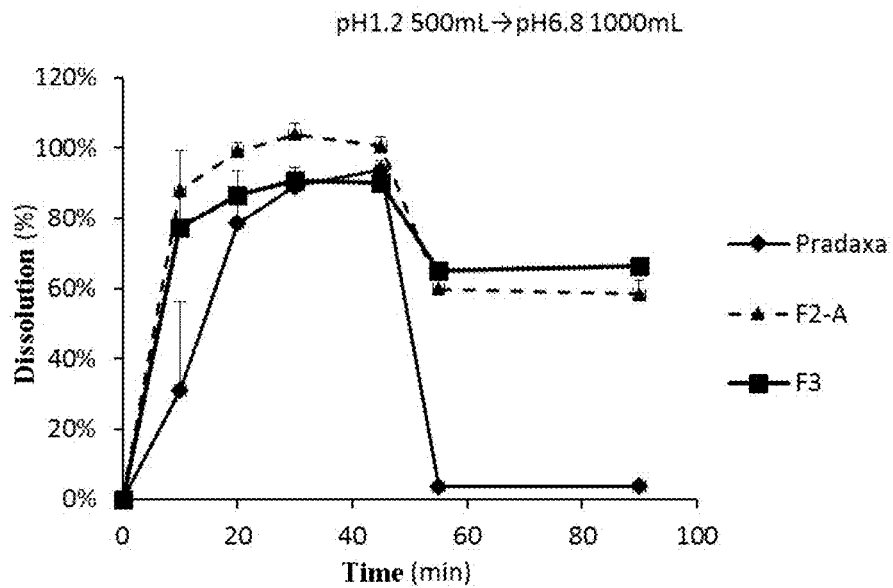
FIG. 13 denotes dissolution profiles of capsules (F3) in Example 8, capsules (F2-A) in Example 7 and the Pradaxa Capsules in a pH 1.2→pH 6.8 two-stage dissolution experiment, wherein the Chinese trade name of the Pradaxa Capsules is Pradaxa, the strength is 150 mg, the manufacturer is Boehringer Ingelheim GmbH, and an error bar represents a standard deviation of n=3.
Figure 14:
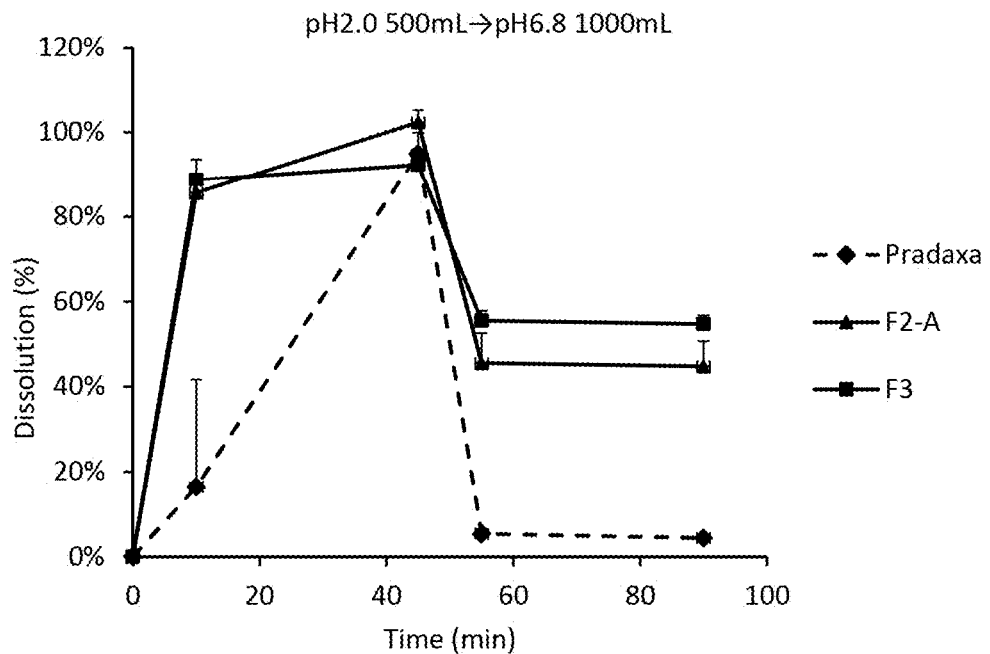
FIG. 14 denotes dissolution profiles of the capsules (F3) in Example 8, the capsules (F2-A) in Example 7 and the Pradaxa Capsules in a pH 2.0→pH 6.8 two-stage dissolution experiment, wherein the Chinese trade name of the Pradaxa Capsules is Pradaxa, the strength is 150 mg, the manufacturer is Boehringer Ingelheim GmbH, and an error bar represents a standard deviation of n=3.
Figure 15:
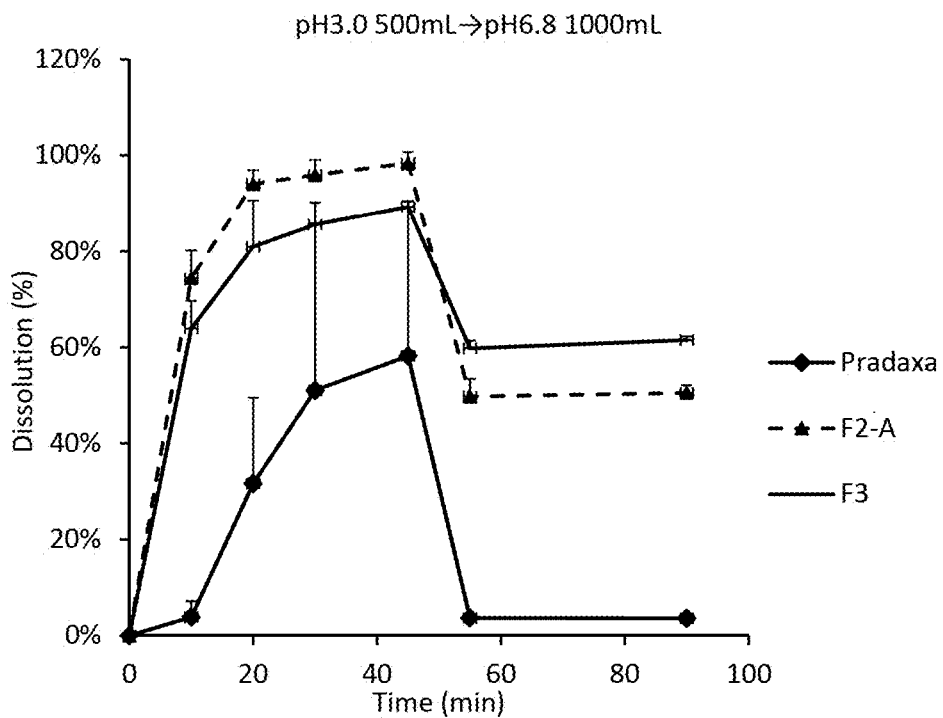
FIG. 15 denotes dissolution profiles of the capsules (F3) in Example 8, the capsules (F2-A) in Example 7 and the Pradaxa Capsules in a pH 3.0→pH 6.8 two-stage dissolution experiment, wherein the Chinese trade name of the Pradaxa Capsules is Pradaxa, the specification is 150 mg, the manufacturer is Boehringer Ingelheim GmbH, and an error bar represents a standard deviation of n=3.

By adopting the test method, dissolution profile of Pradaxa Capsules (150 mg), F2-A and F3 are measured, and results are shown in Table 11, FIG. 13, FIG. 14 and FIG. 15. As can be seen from the results, compared with the Pradaxa Capsules, the preparations (F2-A and F3) of the present disclosure show faster dissolution obviously under acid pH, and precipitations are fewer under neutral pH.

TABLE 11

Dissolution of F3, F2-A and Pradaxa Capsules Changing over Time

| Time (min) | Pradaxa Capsules (150 mg) | | F3 (50 mg) | | F2-A (50 mg) | |
|---|---|---|---|---|---|---|
| | Dissolution/% | SD | Dissolution/% | SD | Dissolution/% | SD |
| pH 1.2 500 mL → pH 6.8 1000 mL | | | | | | |
| 0 | 0.00 | 0.00 | 0.00 | 0.00 | 0.00 | 0.00 |
| 10 | 31.03 | 25.20 | 77.34 | 9.37 | 87.93 | 11.25 |
| 20 | 78.59 | 7.23 | 86.76 | 6.70 | 99.11 | 2.53 |
| 30 | 89.33 | 5.03 | 90.90 | 2.14 | 103.88 | 3.00 |
| 45 | 93.83 | 2.70 | 90.04 | 1.72 | 100.50 | 2.51 |
| 55 | 3.71 | 0.14 | 65.24 | 0.92 | 59.87 | 3.30 |
| 90 | 3.77 | 0.08 | 66.46 | 0.94 | 58.54 | 3.93 |
| pH 2.0 500 mL → pH 6.8 1000 mL | | | | | | |
| 0 | 0.00 | 0.00 | 0.00 | 0.00 | 0.00 | 0.00 |
| 10 | 16.43 | 25.26 | 88.78 | 4.86 | 85.65 | 2.21 |
| 45 | 94.90 | 5.03 | 92.32 | 1.69 | 102.40 | 2.85 |
| 55 | 5.37 | 1.20 | 55.58 | 2.30 | 45.57 | 7.07 |
| 90 | 4.38 | 0.79 | 54.76 | 2.02 | 44.79 | 5.93 |
| pH 3.0 500 mL → pH 6.8 1000 mL | | | | | | |
| 0 | 0.00 | 0.00 | 0.00 | 0.00 | 0.00 | 0.00 |
| 10 | 3.84 | 3.32 | 63.89 | 5.76 | 74.40 | 5.75 |
| 20 | 31.63 | 17.89 | 80.95 | 9.67 | 94.05 | 2.88 |
| 30 | 51.02 | 34.80 | 85.57 | 4.59 | 95.94 | 3.12 |
| 45 | 58.19 | 32.30 | 89.30 | 1.15 | 98.36 | 2.32 |
| 55 | 3.65 | 0.15 | 59.75 | 1.61 | 49.74 | 3.67 |
| 90 | 3.57 | 0.04 | 61.48 | 0.77 | 50.51 | 1.58 |

Example 9

In the example, solid granules in capsules F4 and granules in capsules F5 are prepared through a hot melting granulation process.

Table 12 Compositions of Solid Granules Obtained through Hot Melting Granulation Process in Capsules F4

TABLE 12

Compositions of Solid Granules Obtained through Hot Melting Granulation Process in Capsules F4

| Action | Components | Wt % | Wt/capsule, mg |
|---|---|---|---|
| Amphiphilic Polymer | Soluplus ® Powder | 49.5 | 75.00 |
| Diluting Agent | Mannitol | 24.7 | 37.50 |
| Hydrophilic Polymer | Kolliphor P407 | 19.8 | 30.00 |
| Disintegrating Agent | Croscarmellose sodium | 5.0 | 7.50 |
| Lubricant | Magnesium Stearate | 0.5 | 0.75 |
| Antistatic Agent | Silica | 0.5 | 0.75 |
| / | Total | 100.0 | 151.50 |

TABLE 13

Compositions of Granules Obtained through Hot Melting Granulation Process in Capsules F5

| Action | Compositions | Wt % | Wt/capsule, mg |
|---|---|---|---|
| API | DEM | 16.9 | 57.7 |
| Amphiphilic Polymer | Soluplus ® Powder | 38.8 | 132.5 |
| Diluting Agent | Mannitol | 18.9 | 64.5 |
| Hydrophilic Polymer | Kolliphor P188 | 19.9 | 67.9 |
| Disintegrating Agent | croscarmellose sodium | 5.0 | 17.1 |
| Lubricant | Magnesium Stearate | 0.5 | 1.7 |
| / | Total | 100.0 | 341.4 |

The hot melting granulation process includes the following steps:

Firstly, Soluplus® is milled and screened by a 120-mesh sieve to obtain the Soluplus® powder, and then the Soluplus® powder and the other components except the magnesium stearate are mixed in a glass beaker by a stainless steel spatula at 70 to 75'C according to mass percentages in Table 12 until uniform granules are formed; and afterwards, the granules and the magnesium stearate are mixed to obtain the solid granules in F4.

Firstly, Soluplus® is milled and screened by a 120-mesh sieve to obtain the Soluplus® powder, and then the Soluplus® powder and the other components except the magnesium stearate are mixed in a glass beaker by a stainless steel spatula at 70 to 75'C according to mass percentages in Table 13 until uniform granules are formed; and afterwards, the granules and the magnesium stearate are mixed to obtain the granules in F5.

The pellets F2 (240.3 mg) in Example 7 and the solid granules (151.5 mg) obtained according to a formula of Table 12 are placed into gelatin capsules (#0), and the obtained capsules are recorded as F4. The gelatin capsules (#0) are also filled with the granules (341.4 mg) obtained according to a formula of Table 13 to obtain the capsules F5.

Figure 16:
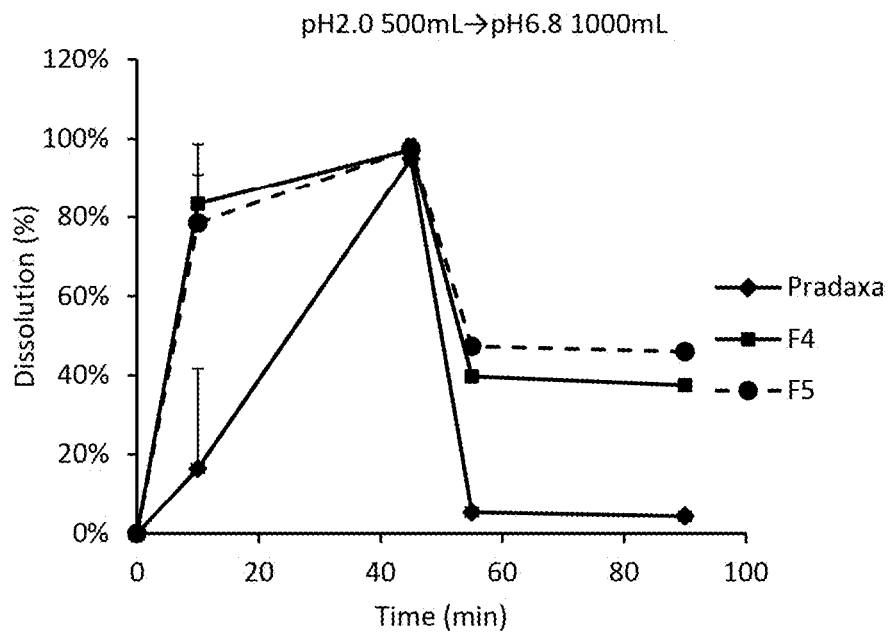
FIG. 16 denotes dissolution profiles of capsules (F4 and F5) in Example 8 and the Pradaxa Capsules in a pH 2.0→pH 6.8 two-stage dissolution experiment, wherein the Chinese trade name of the Pradaxa Capsules is Pradaxa, the specification is 150 mg, the manufacturer is Boehringer Ingelheim GmbH, and an error bar represents a standard deviation of n=3.

The test method which is the same as that in Example 5 is adopted to measure dissolution profile of the capsules F4 and F5, and results are shown in Table 14 and FIG. 16.

As can be seen from Table 14 and FIG. 16, compared with Pradaxa Capsules, the preparations (F4 and F5) of the present disclosure show faster dissolution obviously under acid pH, and precipitations are fewer under neutral pH. The mass percentages of dissolved-out DEM of the Pradaxa Capsules, the F4 and the F5 in the pH 2.0 solution at the $10^{th}$ minute are respectively 16.4%, 83.4% and 78.5%. The mass percentages of dissolved-out DEM of the Pradaxa Capsules, the F4 and the F5 in the pH 6.8 solution at the $10^{th}$ minute are respectively 5.4%, 39.7% and 47.4%.

TABLE 14

Dissolution of F4, F5 and Pradaxa Capsules in Example 9 Changing over Time

| Time (min) | Pradaxa Capsules (150 mg) | | F4 (50 mg) | | F5 (50 mg) | |
|---|---|---|---|---|---|---|
| | Dissolution/% | SD/% | Dissolution/% | SD/% | Dissolution/% | SD/% |
| pH 2.0 500 mL → pH 6.8 1000 mL | | | | | | |
| 0 | 0.00 | 0.00 | 0.00 | 0.00 | 0.00 | 0.00 |
| 10 | 16.43 | 25.26 | 83.36 | 15.22 | 78.50 | 12.36 |
| 45 | 94.90 | 5.03 | 97.21 | 1.18 | 97.42 | 0.64 |

TABLE 14-continued

Dissolution of F4, F5 and Pradaxa Capsules in Example 9 Changing over Time

| Time (min) | Pradaxa Capsules (150 mg) | | F4 (50 mg) | | F5 (50 mg) | |
|---|---|---|---|---|---|---|
| | Dissolution/% | SD % | Dissolution/% | SD % | Dissolution/% | SD % |
| | pH 2.0 500 mL → pH 6.8 1000 mL | | | | | |
| 55 | 5.37 | 1.20 | 39.73 | 0.65 | 47.35 | 0.96 |
| 90 | 4.38 | 0.79 | 37.49 | 0.28 | 45.99 | 0.66 |

Example 10

A hot melting granulation process includes the following steps:

Firstly, Soluplus® is milled and screened by a 120-mesh sieve to obtain the Soluplus® powder, and then the Soluplus® powder and other components except magnesium stearate and externally-added croscarmellose sodium are mixed in a glass beaker by a stainless steel spatula at 70 to 75° C. according to mass percentages in Table 15 until uniform granules are formed; afterwards, the granules, the magnesium stearate and the externally-added croscarmellose sodium are mixed to obtain granules in F10; and gelatin capsules (#0) are filled with the granules obtained according to a formula of Table 15 to obtain the capsules F10.

Firstly, Soluplus® is milled and screened by a 120-mesh sieve to obtain the Soluplus® powder, and then the Soluplus® powder and other components except magnesium stearate and externally-added low-substituted hydroxypropyl cellulose are mixed in a glass beaker by a stainless steel spatula at 70 to 75° C. according to mass percentages in Table 16 until uniform granules are formed; afterwards, the granules, the magnesium stearate and the externally-added low-substituted hydroxypropyl cellulose are mixed to obtain granules in F11; and gelatin capsules (#0) are filled with the granules obtained according to a formula of Table 16 to obtain the capsules F11.

TABLE 15

Compositions of Granules F10 Obtained through Hot Melting Granulation Process

| Action | Compositions | Mg/granule | Percentage % |
|---|---|---|---|
| API | DEM | 173.4 | 43.35 |
| Amphiphilic Polymer | Soluplus ® Powder | 40.0 | 10.00 |
| Diluting Agent | Mannitol | 36.0 | 9.00 |
| Hydrophilic Polymer | Kolliphor P407 | 88.6 | 22.15 |
| Disintegrating Agent | Internally-added croscarmellose sodium | 20.0 | 5 |
| Disintegrating Agent | Externally-added croscarmellose sodium | 40.0 | 10 |
| Lubricant | Magnesium Stearate | 2.0 | 0.5 |
| / | Total | 400 | 100 |

TABLE 16

Compositions of Granules F11 Obtained through Hot Melting Granulation Process

| Action | Compositions | Mg/granule | Percentage % |
|---|---|---|---|
| API | DEM | 173.4 | 43.35 |
| Amphiphilic Polymer | Soluplus ® Powder | 40.0 | 10.00 |
| Diluting Agent | Mannitol | 36.0 | 9.00 |
| Hydrophilic Polymer | Kolliphor P407 | 88.6 | 22.15 |
| Disintegrating Agent | Internally-added Low-substituted Hydroxypropyl Cellulose | 20.0 | 5 |
| Disintegrating Agent | Externally-added Low-substituted Hydroxypropyl Cellulose | 40.0 | 10 |
| Lubricant | Magnesium Stearate | 2.0 | 0.5 |
| / | Total | 400 | 100 |

Figure 17:
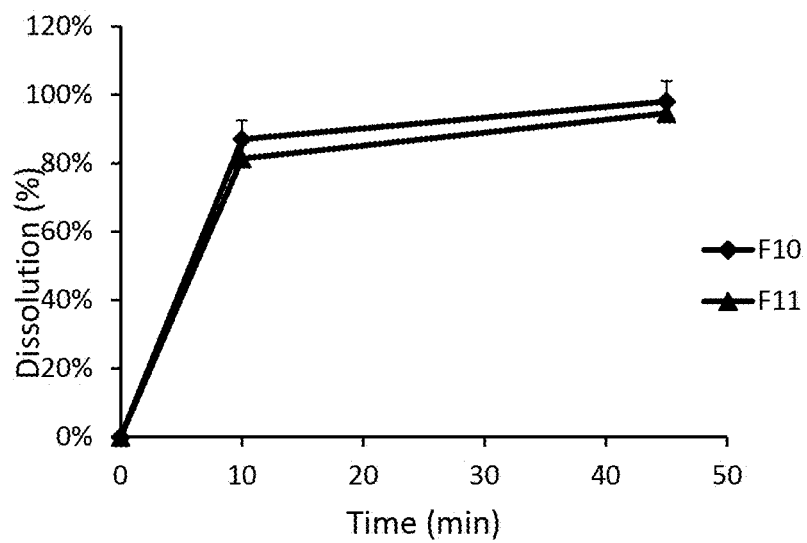
FIG. 17 denotes dissolution profiles of capsules (F10 and F11) respectively containing two disintegrating agents in a pH 2.0 hydrochloric acid solution in Example 10, wherein an error bar represents a standard deviation of n=3.

F10 and F11 are placed into the pH 2.0 solution to measure dissolution profile, and results are shown in Table 17 and FIG. 17. As can be seen from Table 17 and FIG. 17, dissolution results of the two dosage forms F10 and F11 have no remarkable difference.

TABLE 17

Dissolution of F10 and F11 in Example 10 Changing over Time

| Time (min) | F10 (150 mg) | | F11 (150 mg) | |
|---|---|---|---|---|
| | Dissolution/% | SD % | Dissolution/% | SD % |
| | pH 2.0 500 mL → pH 6.8 1000 mL | | | |
| 0 | 0.00 | 0.00 | 0.00 | 0.00 |
| 10 | 87.07 | 5.48 | 81.48 | 5.53 |
| 45 | 98.05 | 6.12 | 94.65 | 4.47 |

Example 11

According to Table 18, pellets are prepared by spraying a solid dispersion composition to neutral cores, and the solid dispersion composition is composed of following components in percentage by mass: 40 wt % of DEM, 10 wt % of Soluplus®, and 50 wt % of Kolliphor® P407.

A specific preparation method is as follows:

Preparation of the pellets: The solid dispersion composition is dissolved in a mixed solution of 90 wt % of ethanol and 10 wt % of deionized water to prepare a coating solution, wherein the coating solution contains 24 wt % of the solid dispersion composition. Then, the neutral cores (300 to 500 μm) are pre-dried in an 80° C. convection oven until the moisture content of the neutral cores is lower than 1.0%.

Afterwards, 104.2 g of the coating solution containing 25 g of the solid dispersion composition is sprayed to 50 g of the pre-dried sugar spheres on a fluidized bed granulator with a Wurster insert under proper inlet air pressure and the 45 to 50° C. air inlet temperature, and in a spraying process, the spraying speed and atomization pressure are adjusted to enable the product temperature to be kept at 30 to 50° C. After the coating solution is used up, a product is dried in a fluidized bed until the moisture content is lower than 1.0%, and a target mass ratio of solid dispersion layers wrapping the neutral cores to the neutral cores is 0.5/1.0, so that drug granules are obtained.

Preparation of Soluplus® powder: Firstly Soluplus® granules are milled and then screened by an 80-mesh sieve to obtain Soluplus® powder (less than 80 meshes). The drug granules (pellets) and the Soluplus® powder are mixed to obtain the pellets (formulations) in Example 11.

TABLE 18

Compositions of Pellets F6

| Name | Action | Components | Wt/% | Wt/capsule, mg |
|---|---|---|---|---|
| | | Drug Granule Composition | | |
| Solid Dispersion Composition | API | DEM | 13.3 | 57.7 |
| | Amphiphilic Polymer | Soluplus ® | 3.33 | 14.4 |
| | Hydrophilic Polymer | Kolliphor P407 | 16.7 | 72.1 |
| Neutral Cores | / | Sugar Spheres | 66.7 | 288.5 |
| | / | Total | 100.0 | 432.7 |
| Solid Granules | Amphiphilic Polymer | Soluplus ® Powder | 100.0 | 120.0 |

Test Method:

The difference from the test method in Example 5 is that pH of the first stage is set as 2.0 or 6.0 (namely acid media adopted in the first stage are respectively: the pH 2.0 solution and the pH 6.0 solution), and other aspects are the same as the test method in Example 5.

Figure 18:
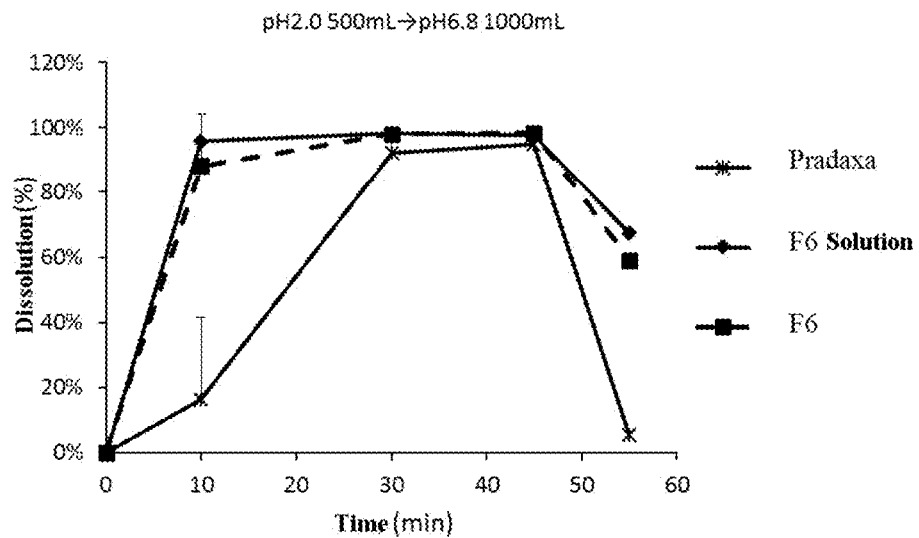
FIG. 18 denotes dissolution profiles of pellets (F6) in Example 11, a solution or suspension (F6 solution) obtained after dispersion of the pellets (F6) and the Pradaxa Capsules in a pH 2.0→pH 6.8 two-stage dissolution experiment, wherein the Chinese trade name of the Pradaxa Capsules is Pradaxa, the strength is 150 mg, the manufacturer is Boehringer Ingelheim GmbH, and an error bar represents a standard deviation of n=3.
Figure 19:
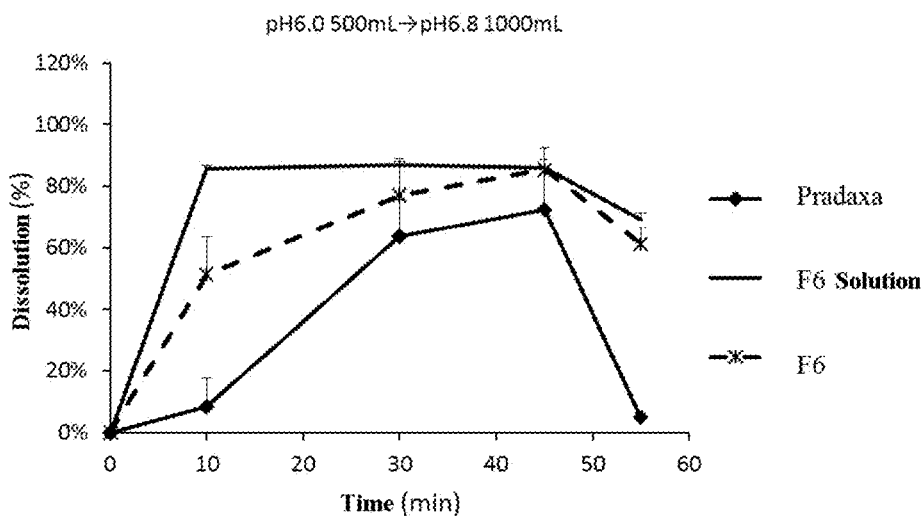
FIG. 19 denotes dissolution profiles of the pellets (F6) in Example 11, the solution or suspension (F6 solution) obtained after dispersion of the pellets (F6) and the Pradaxa Capsules in a pH 6.0→pH 6.8 two-stage dissolution experiment, wherein the Chinese trade name of the Pradaxa Capsules is Pradaxa, the strength is 150 mg, the manufacturer is Boehringer Ingelheim GmbH, and an error bar represents a standard deviation of n=3.

By adopting the above test method, dissolution profile of the pellets F6 are measured. For comparison, the pellets F6 are pre-dissolved in 25 mL of deionized water to obtain an F6 solution, dissolution profile of the F6 solution are measured through the same method, and results are shown in Table 19, FIG. 18 and FIG. 19.

As can be seen from the results, compared with Pradaxa Capsules, F6 shows faster dissolution under acid pH 2 and pH 6, and precipitations are fewer under neutral pH 6.8. F6 may prevent 60% or more of dissolved-out DEM in the acid media (pH 2.0 and pH 6.0) from being precipitated. At the room temperature, the F6 solution may promote dissolution of the DEM and the Soluplus®, and therefore, the better precipitation inhibition effect is generated under neutral pH (pH 6.8).

TABLE 19

Dissolution of F6 and Pradaxa Capsules in Example 11 Changing over Time

| | Pradaxa Capsules (150 mg) | | F6 (50 mg) | | F6 Solution (50 mg) | |
|---|---|---|---|---|---|---|
| Time (min) | Dissolution/% | SD | Dissolution/% | SD | Dissolution/% | SD |
| pH 2.0 500 mL → pH 6.8 1000 mL | | | | | | |
| 0 | 0.00 | 0.00 | 0.00 | 0.00 | 0.00 | 0.00 |
| 10 | 16.43 | 25.26 | 88.24 | 7.32 | 96.01 | 8.05 |
| 30 | 92.17 | 7.23 | 98.03 | 1.25 | 98.27 | 1.28 |
| 45 | 94.90 | 5.03 | 98.37 | 0.71 | 97.78 | 0.75 |
| 55 | 5.37 | 1.20 | 59.03 | 1.26 | 67.49 | 0.65 |
| pH 6.0 500 mL → pH 6.8 1000 mL | | | | | | |
| 0 | 0.00 | 0.00 | 0.00 | 0.00 | 0.00 | 0.00 |
| 10 | 8.47 | 9.05 | 51.31 | 12.08 | 85.70 | 1.09 |
| 30 | 63.63 | 12.18 | 77.19 | 10.91 | 86.85 | 2.17 |
| 45 | 72.60 | 13.09 | 85.38 | 6.91 | 86.05 | 2.57 |
| 55 | 4.94 | 0.11 | 61.30 | 5.28 | 69.33 | 2.20 |

Example 12

A preparation method of acid-core pellets is as follows:

According to Table 20, an isolation layer composition (the composition includes in percentage by mass: 67% of Soluplus® and 33% of Kolliphor® P407) is dissolved in a mixed solution of 95 wt % of ethanol and 5 wt % of deionized water to prepare a coating solution, wherein the coating solution contains 26% of the isolation layer composition by mass.

Afterwards, tartaric acid cores (300 to 500 μm) are pre-dried in an 80° C. convection oven until the moisture content of the tartaric acid cores is lower than 1.00%.

Then, the coating solution containing 20 g of the isolation layer composition is sprayed to 50 g of the pre-dried tartaric acid cores on a fluidized bed granulator with a Wurster insert under proper inlet air pressure and the 35° C. air inlet temperature, and in a spraying process, the spraying speed and atomization pressure are adjusted to enable the product temperature to be kept at 30 to 32° C. After the coating solution is used up, a product is dried in a fluidized bed until the moisture content is lower than 1.0% (if the moisture content is not lower than 1.0% after drying in the fluidized bed, a secondary drying process in the oven is necessary), and a target mass ratio of isolation layers to the tartaric acid cores is 0.4/1.0.

A coating process of a drug layer composition is the same as that in Example 11. The drug layer composition is composed of following components in percentage by mass: 28.9 wt % of DEM, 25.9 wt % of Soluplus® and 45.3 wt % of Kolliphor® P407. A target mass ratio of drug layers to the tartaric acid cores wrapped with the isolation layers is 1.0/1.0.

TABLE 20

Compositions of Acid-core Pellets F7

| Action | Components | Wt % | Wt/capsule, mg |
|---|---|---|---|
| Tartaric Acid Cores | | | |
| Acid Core | Tartaric Acid | 35.7 | 142.8 |
| Isolation Layer Composition | | | |
| Amphiphilic Polymer | Soluplus ® | 9.6 | 38.3 |
| Hydrophilic Polymer | Kolliphor P407 | 4.7 | 18.9 |
| Drug Layer Composition | | | |
| API | DEM | 14.4 | 57.7 |
| Amphiphilic Polymer | Soluplus ® | 12.9 | 51.7 |
| Hydrophilic Polymer | Kolliphor P407 | 22.6 | 90.6 |
| / | Total | 100.0 | 399.9 |

Test Method:

The difference from the test method in Example 5 is that pH of the first stage is set as 2.0 or 6.0 (namely acid media adopted in the first stage are respectively: the pH 2.0 solution and the pH 6.0 solution), and other aspects are the same as the test method in Example 5.

Figure 20:
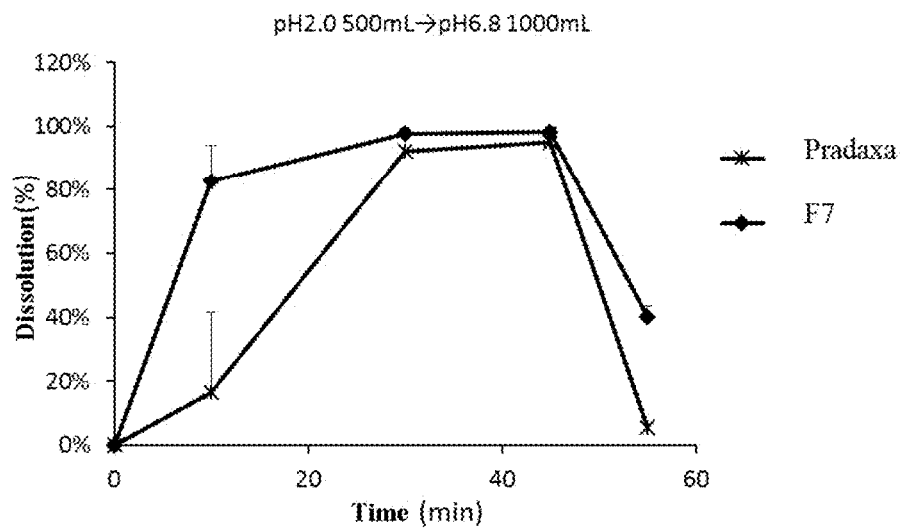
FIG. 20 denotes dissolution profiles of acid-core pellets (F7) in Example 12 and the Pradaxa Capsules in a pH 2.0→pH 6.8 two-stage dissolution experiment, wherein the Chinese trade name of the Pradaxa Capsules is Pradaxa, the strength is 150 mg, the manufacturer is Boehringer Ingelheim GmbH, and an error bar represents a standard deviation of n=3.
Figure 21:
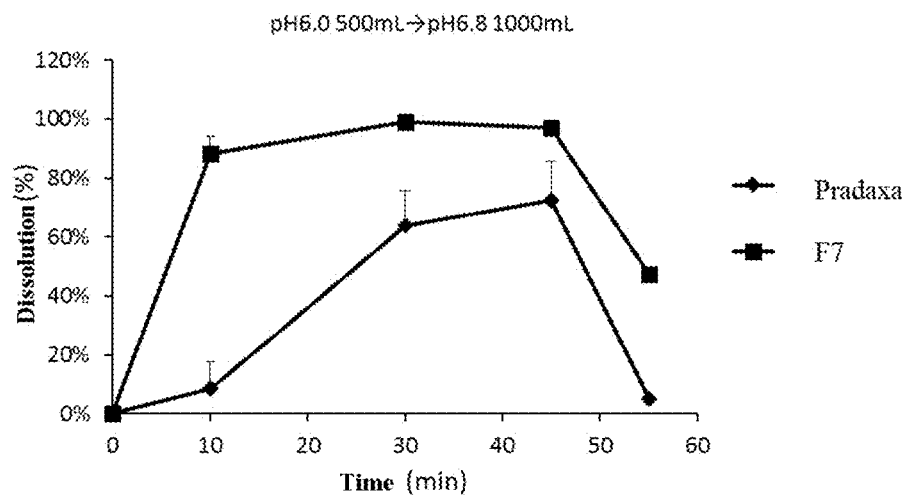
FIG. 21 denotes dissolution profiles of the acid-core pellets (F7) in Example 12 and the Pradaxa Capsules in a pH 6.0→pH 6.8 two-stage dissolution experiment, wherein the Chinese trade name of the Pradaxa Capsules is Pradaxa, the strength is 150 mg, the manufacturer is Boehringer Ingelheim GmbH, and an error bar represents a standard deviation of n=3.

Through the test method, dissolution profile of F7 are measured, and results are shown in Table 21, FIG. 20 and FIG. 21.

As can be seen from the results, the DEM may be quickly dissolved out of F7, F7 may enhance a dissolution rate under acid environment (pH 6.0), and 40% to 47% of the DEM which has been dissolved out in acid environment (pH 2.0 and pH 6.0) will not precipitate under neutral pH (pH 6.8).

TABLE 21

Dissolution of F7 and Pradaxa Capsules in Example 12 Changing over Time

| Time (min) | Pradaxa Capsules (150 mg) Dissolution/% | SD | F7 (50 mg) Dissolution/% | SD |
|---|---|---|---|---|
| | pH 2.0 500 mL → pH 6.8 1000 mL | | | |
| 0 | 0.00 | 0.00 | 0.00 | 0.00 |
| 10 | 16.43 | 25.26 | 82.65 | 11.24 |
| 30 | 92.17 | 7.23 | 97.69 | 1.32 |
| 45 | 94.90 | 5.03 | 98.29 | 1.13 |
| 55 | 5.37 | 1.20 | 40.28 | 3.31 |
| | pH 6.0 500 mL → pH 6.8 1000 mL | | | |
| 0 | 0.00 | 0.00 | 0.00 | 0.00 |
| 10 | 8.47 | 9.05 | 88.13 | 5.88 |
| 30 | 63.63 | 12.18 | 99.01 | 2.08 |
| 45 | 72.60 | 13.09 | 96.96 | 2.03 |
| 55 | 4.94 | 0.11 | 47.47 | 2.28 |

Example 13

A hot melting granulation process includes the following steps:

Firstly, Soluplus® is milled and screened by a 120-mesh sieve to obtain the Soluplus® powder, and then the Soluplus® powder and other components except magnesium stearate and externally-added croscarmellose sodium are mixed in a glass beaker by a stainless steel spatula at 70 to 75° C. according to mass percentages in Table 22 until uniform granules are formed. Afterwards, the above granules, the magnesium stearate and the externally-added croscarmellose sodium are mixed to obtain granules in F8. Gelatin capsules (#0) are filled with the granules obtained according to a formula of Table 22 to obtain capsules F8.

TABLE 22

Compositions of Granules F8 Obtained through Hot Melting Granulation Process

| | | Number WD-033177-B | |
|---|---|---|---|
| Action | Compositions | Mg/granule | Percentage % |
| API | DEM | 173.4 | 39.1 |
| Amphiphilic Polymer | Soluplus ® Powder | 40.8 | 9.2 |
| Diluting Agent | Mannitol | 40.8 | 9.2 |
| Hydrophilic Polymer | Kolliphor P188 | 85.0 | 19.2 |
| Disintegrating Agent | Internally-added croscarmellose sodium | 17.0 | 3.8 |
| | Total | 357 | 80.4 |
| Lubricant | Magnesium Stearate | 1.8 | 0.4 |
| Disintegrating Agent | Externally-added croscarmellose sodium | 85.0 | 19.2 |
| | Total | 443.8 | 100.0 |

Figure 22:
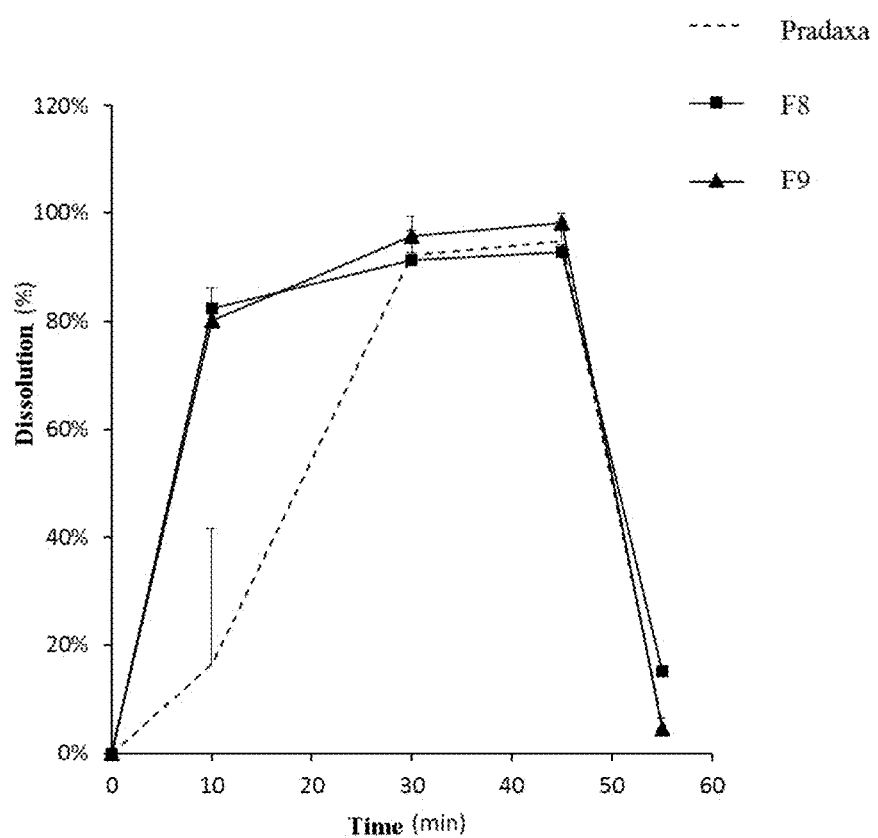
FIG. 22 denotes dissolution profiles of capsules (F8 and F9) and the Pradaxa Capsules in a pH 2.0→pH 6.8 two-stage dissolution experiment in Example 13 and Comparative Example 1, wherein the Chinese trade name of the Pradaxa Capsules is Pradaxa, the strength is 150 mg, the manufacturer is Boehringer Ingelheim GmbH, and an error bar represents a standard deviation of n=3.

The test method which is the same as that in Example 5 is adopted to measure dissolution profile of F8, and results are shown in Table 23 and FIG. 22.

TABLE 23

Dissolution of F8 in Example 13 and F9 and Pradaxa Capsules in Comparative Example 1 Changing over Time

| | Pradaxa Capsules (150 mg) | | F8 (150 mg) | | F9 (150 mg) | |
|---|---|---|---|---|---|---|
| Time (min) | Dissolution/% | SD | Dissolution/% | SD | Dissolution/% | SD |
| | pH 2.0 500 mL → pH 6.8 1000 mL | | | | | |
| 0 | 0.00 | 0.00 | 0.00 | 0.00 | 0.00 | 0.00 |
| 10 | 16.43 | 25.26 | 82.30 | 1.18 | 80.10 | 6.03 |
| 30 | 92.17 | 7.23 | 91.35 | 1.33 | 95.83 | 1.01 |
| 45 | 94.90 | 5.03 | 92.78 | 1.46 | 98.17 | 0.25 |
| 55 | 5.37 | 1.20 | 15.12 | 0.19 | 4.54 | 0.14 |

Example 14

In the example, stability research is performed on two representative formulas (F4 and F5), namely the pellet formula and the hot melting granulation formula.

F4 and F5 are packaged in HDPE bottles and then stored under the conditions that the temperature is 40° C. and the relative humidity is 75% for 6 months.

The before-mentioned pH 2.0→pH 6.8 two-stage dissolution method is adopted to detect dissolution behaviors of samples. HPLC is adopted to detect the impurity content of the samples. A Karl-Fischer method is adopted to detect the moisture content.

Results show that after the samples are stored under the conditions that the temperature is 40° C. and the relative humidity is 75% for 6 months, the dissolution behaviors and DEM content of the samples have no remarkable change, the impurity content is within a mass index limit range, and the moisture content meets requirements of mass indexes.

Comparative Example 1

A hot melting granulation process includes the following steps:

Other components except magnesium stearate and externally-added croscarmellose sodium are mixed in a glass beaker by a stainless steel spatula under 70 to 75° C. until uniform granules are formed. Then the above granules, the magnesium stearate and the externally-added croscarmellose sodium are mixed to obtain granules in F9. Gelatin capsules (#0) are filled with the granules obtained according to a formula of Table 24 to obtain capsules F9.

TABLE 24

Compositions of Granules F9 Obtained through Hot Melting Granulation Process

| | | Number WD-033188-A | |
|---|---|---|---|
| Action | Compositions | Mg/granule | Percentage % |
| API | DEM | 173.4 | 39.1 |
| Amphiphilic Polymer | Soluplus ® | 0 | 0 |
| Diluting Agent | Mannitol | 81.6 | 18.4 |
| Hydrophilic Polymer | Kolliphor P188 | 85.0 | 19.2 |
| Disintegrating Agent | Internally-added croscarmellose sodium | 17.0 | 3.8 |
| | Total | 357 | 80.4 |

TABLE 24-continued

Compositions of Granules F9 Obtained through Hot Melting Granulation Process

| | | Number WD-033188-A | |
|---|---|---|---|
| Action | Compositions | Mg/ granule | Percentage % |
| Lubricant | Magnesium stearate | 1.8 | 0.4 |
| Disintegrating Agent | Externally-added croscarmellose sodium | 85.0 | 19.2 |
| | Total | 443.8 | 100.0 |

The test method which is the same as that in Example 5 is adopted to measure dissolution profile of F9, and results are shown in FIG. 22.

It can be seen from FIG. 22 that the precipitation condition of a formula (F9) containing no Soluplus® under pH 6.8 is close to that of existing commercially-available originally-researched products, and a formula (F8) with the Soluplus® added may remarkably improve the concentration of DEM under pH 6.8.

What is claimed is:

1. A pharmaceutical composition containing dabigatran etexilate, comprising an active pharmaceutical ingredient and an amphiphilic polymer, wherein
the active pharmaceutical ingredient is dabigatran etexilate and/or dabigatran etexilate mesylate, the amphiphilic polymer is polyvinyl caprolactam-polyvinyl acetate-polyethylene glycol graft copolymer, and a mass ratio of the active pharmaceutical ingredient to the amphiphilic polymer is 1:0.23 to 1:3;
the pharmaceutical composition further comprises a hydrophilic polymer, the hydrophilic polymer is polyoxyethylene-polyoxypropylene glycol block copolymer;
a mass percentage of the active pharmaceutical ingredient in the pharmaceutical composition is 5 wt % to 60 wt %; a mass percentage of the amphiphilic polymer in the pharmaceutical composition is 3 wt % to 40 wt %; and a mass percentage of the hydrophilic polymer in the pharmaceutical composition is 10 wt % to 90 wt %; and
the active pharmaceutical ingredient, the amphiphilic polymer and the hydrophilic polymer in the pharmaceutical composition form a solid dispersion.

2. The pharmaceutical composition containing dabigatran etexilate as defined in claim 1, wherein
a mass of the active pharmaceutical ingredient in the pharmaceutical composition is 30 to 180 mg;
or, the number of repeat units of vinyl caprolactam in the amphiphilic polymer is 57 or below;
or, the number of repeat units of vinyl acetate in the amphiphilic polymer is 30 or below;
or, the number of repeat units of polyethylene glycol in the amphiphilic polymer is 13 or above;
or, monomers in the amphiphilic polymer are polyethylene glycol 6000, vinyl caprolactam and vinyl acetate, and a mole ratio of the three monomers, namely the polyethylene glycol 6000, the vinyl caprolactam and the vinyl acetate, in the amphiphilic polymer is 13:57:30;
or, a molecular weight of the amphiphilic polymer is 90,000 to 140,000 g/mol;
or, a glass transition temperature of the amphiphilic polymer is 69 to 71° C.;
or, the mass ratio of the active pharmaceutical ingredient to the amphiphilic polymer is 1:0.24 to 1:3.

3. The pharmaceutical composition containing dabigatran etexilate as defined in claim 1, wherein
the pharmaceutical composition further comprises a disintegrating agent;
or, the pharmaceutical composition further comprises an antistatic agent;
or, the pharmaceutical composition further comprises a lubricant;
or, the pharmaceutical composition further comprises a diluent.

4. The pharmaceutical composition containing dabigatran etexilate as defined in claim 1, wherein the pharmaceutical composition comprises the components of following mass fraction: 13% to 44% of the active pharmaceutical ingredient, 6% to 39% of the amphiphilic polymer, 16% to 36% of a hydrophilic polymer, 9% to 39% of a diluent, 5% to 23% of a disintegrating agent and 0.4% to 0.5% of a lubricant;
wherein, the diluent is mannitol or lactose monohydrate;
the disintegrating agent is one or more selected from the group consisting of croscarmellose sodium, low-substituted hydroxypropyl cellulose, sodium starch glycolate and crospovidone;
the antistatic agent is one or more selected from the group consisting of long-chained alkylphenol, ethoxylated amine, glyceride and silica;
the lubricant is one or more selected from the group consisting of calcium stearate, glyceryl behenate, magnesium stearate, sodium stearyl fumarate, talcum powder, colloidal silica, magnesium silicate and calcium silicate.

5. The pharmaceutical composition containing dabigatran etexilate as defined in claim 1, wherein,
the pharmaceutical composition is composed of the components of following mass fraction: 16.9% of dabigatran etexilate mesylate, 38.8% of polyvinyl caprolactam-polyvinyl acetate-polyethylene glycol graft copolymer, 18.9% of mannitol, 19.9% of polyoxyethylene-polyoxypropylene glycol block copolymer P188, 5.0% of croscarmellose sodium and 0.5% of magnesium stearate;
or, the pharmaceutical composition is composed of the components of following mass fraction: 43.35% of dabigatran etexilate mesylate, 10% of polyvinyl caprolactam-polyvinyl acetate-polyethylene glycol graft copolymer, 9% of mannitol, 22.15% of polyoxyethylene-polyoxypropylene glycol block copolymer P407, 15.0% of croscarmellose sodium and 0.5% of magnesium stearate;
or, the pharmaceutical composition is composed of the components of following mass fraction: 43.35% of dabigatran etexilate mesylate, 10% of polyvinyl caprolactam-polyvinyl acetate-polyethylene glycol graft copolymer, 9% of mannitol, 22.15% of polyoxyethylene-polyoxypropylene glycol block copolymer P407, 15.0% of low-substituted hydroxypropyl cellulose and 0.5% of magnesium stearate;
or, the pharmaceutical composition is composed of the components of following mass fraction: 39.1% of dabigatran etexilate mesylate, 9.2% of polyvinyl caprolactam-polyvinyl acetate-polyethylene glycol graft copolymer, 9.2% of mannitol, 19.2% of polyoxyethylene-polyoxypropylene glycol block copolymer P188, 23.0% of croscarmellose sodium and 0.4% of magnesium stearate.

6. The pharmaceutical composition containing dabigatran etexilate as defined in claim 1, wherein the pharmaceutical composition exists in the following forms: powder, pellets, granules, capsules or tablets; and the pellet is divided into a neutral-core pellet and an acid-core pellet according to the difference of core thereof.

7. The pharmaceutical composition containing dabigatran etexilate as defined in claim 6, wherein, when the pharmaceutical composition exists in the form of powder, a method for preparing the powder comprises following steps: dissolving all the components of the pharmaceutical composition in an ethanol aqueous solution, and carrying out spray-drying;

when the pharmaceutical composition exists in the form of the neutral-core pellet, the neutral-core pellet is provided with a neutral core and drug layers wrapping the neutral core, a method for preparing the neutral-core pellet comprises following steps: dissolving all the components of the pharmaceutical composition in an ethanol aqueous solution, and spraying the obtained solution to the neutral core;

when the pharmaceutical composition exists in the form of an acid-core pellet, the acid-core pellet comprises an acid core, isolation layer and drug layer, the isolation layer wraps the surface of the acid core, and the drug layer wraps the surface of the isolation layer; and the isolation layer comprises polyvinyl caprolactam-polyvinyl acetate-polyethylene glycol graft copolymer and polyoxyethylene-polyoxypropylene glycol block copolymer P407;

when the pharmaceutical composition exists in the form of granules, a method for preparing the granules is wet granulation, rolling granulation, fluidized bed granulation or hot melting granulation.

8. The pharmaceutical composition containing dabigatran etexilate as defined in claim 6, wherein the pharmaceutical composition exists in the forms of powder, pellets, granules, capsules or tablets; and the active pharmaceutical ingredient and other components in the pharmaceutical composition jointly form a solid dispersion.

9. The pharmaceutical composition containing dabigatran etexilate as defined in claim 6, wherein the pharmaceutical composition exists in the forms of powder, pellets, granules, capsules or tablets, the amphiphilic polymer in the pharmaceutical composition exists in two forms simultaneously, the first form is that the amphiphilic polymer and the active pharmaceutical ingredient form a solid dispersion, and the second form is that the amphiphilic polymer exists in a form of solid granules.

10. The pharmaceutical composition containing dabigatran etexilate as defined in claim 9, wherein the solid granule of the amphiphilic polymer comprises the components of following mass fraction: 40% to 58% of the amphiphilic polymer, 0% to 55% of a hydrophilic polymer, 0% to 55% of a diluent, 5% to 20% of a disintegrating agent, 0% to 5% of an antistatic agent and 0% to 2% of a lubricant;

or, the solid granule of the amphiphilic polymer comprises the components of following mass fraction: 41.9% to 50% of the amphiphilic polymer, 19.8% to 51.9% of hydrophilic polymer, 24.7% to 51.9% of a diluent, 5.0% to 5.25% of a disintegrating agent, 0.1% to 1% of an antistatic agent and 0.1% to 1% of a lubricant;

wherein or lactose monohydrate;

the disintegrating agent is one or more selected from the group consisting of croscarmellose sodium, low-substituted hydroxypropyl cellulose, sodium starch glycolate and crospovidone;

the antistatic agent is one or more selected from the group consisting of long-chained alkylphenol, ethoxylated amine, glyceride and silica;

the lubricant is one or more selected from the group consisting of calcium stearate, glyceryl behenate, magnesium stearate, sodium stearyl fumarate, talcum powder, colloidal silica, magnesium silicate and calcium silicate.

11. The pharmaceutical composition containing dabigatran etexilate as defined in claim 10, wherein a method for preparing the solid granule is wet granulation, rolling granulation, fluidized bed granulation or hot melting granulation; or a method for preparing the solid granule is hot melting granulation; or a solvent adopted in the wet granulation is isopropanol.

12. A method for preparing the pharmaceutical composition as defined in claim 1, wherein when the pharmaceutical composition does not contain a neutral core and exists in a form of powder, the method for preparing the powder comprises the following steps: dissolving all components of the pharmaceutical composition in an ethanol aqueous solution, and carrying out spray-drying;

when the pharmaceutical composition does not contain a neutral core and exists in a form of a granule, the method for preparing the granule comprises the following steps: with isopropanol as a granulation solvent, carrying out wet granulation on a mixture of all components of the pharmaceutical composition to obtain wet granule; and then carrying out drying after the wet granule is sieved by a 20-mesh sieve;

when the pharmaceutical composition contains a neutral core and exists in a form of a neutral-core pellet, the method for preparing the neutral-core pellet comprises the following steps: spraying a coating solution to the neutral core, wherein the coating solution is formed by dissolving other components in the pharmaceutical composition except the neutral core into an organic solvent, the neutral core is pre-dried neutral core;

when the pharmaceutical composition contains an acid core and exists in a form of an acid-core pellet, the method for preparing the acid-core pellet comprises the following steps: (1) spraying a coating solution to the acid core to obtain an acid granule, wherein the coating solution is formed by dissolving all components of an isolation layer in an organic solvent; and (2) spraying a coating solution to the acid granule, wherein the coating solution is formed by dissolving all components of a drug layer in an organic solvent; in step (1), the acid core is pre-dried acid core.

13. The pharmaceutical composition containing dabigatran etexilate as defined in claim 2, wherein, the mass of the active pharmaceutical ingredient in the pharmaceutical composition is 39.1 to 173 mg;

or, the mass ratio of the active pharmaceutical ingredient to the amphiphilic polymer is 1:0.24, 1:0.25, 1:0.33, 1:0.77, 1:1, 1:1.2, 1:1.5, 1:1.6, 1:2, or 1:2.3.

14. The pharmaceutical composition containing dabigatran etexilate as defined in claim 1, wherein, the polyoxyethylene-polyoxypropylene glycol block copolymer is polyoxyethylene-polyoxypropylene glycol block copolymer P188 or polyoxyethylene-polyoxypropylene glycol block copolymer P407;

the mass percentage of the active pharmaceutical ingredient in the pharmaceutical composition is 10 wt % to 55 wt %;

or, the mass percentage of the amphiphilic polymer in the pharmaceutical composition is 3.3 wt %, 6.0 wt %, 9.2 wt %, 10.0 wt %, 12.8 wt %, 12.9 wt %, 18.6 wt %, 21.3 wt %, 22.5 wt %, 22.8 wt %, 24.3 wt %, 28.3 wt %, 38.8 wt % or 39.2 wt %;

or, the mass percentage of the hydrophilic polymer in the pharmaceutical composition is 20 wt % to 80 wt %.

15. The pharmaceutical composition containing dabigatran etexilate as defined in claim 3, wherein, when the pharmaceutical composition comprises a disintegrating agent, then the disintegrating agent is one or more selected from the group consisting of croscarmellose sodium, low-substituted hydroxypropyl cellulose, sodium starch glycolate and crospovidone; or a mass percentage of the disintegrating agent in the pharmaceutical composition is 0 wt % to 5 wt % excluding 0 wt %;

or, when the pharmaceutical composition comprises an antistatic agent, then the antistatic agent is one or more selected from the group consisting of long-chained alkylphenol, ethoxylated amine, glyceride and silica; or a mass percentage of the antistatic agent in the pharmaceutical composition is 0 wt % to 5 wt % excluding 0 wt %;

or, when the pharmaceutical composition comprises a lubricant, then the lubricant is one or more selected from the group consisting of calcium stearate, glyceryl behenate, magnesium stearate, sodium stearyl fumarate, talcum powder, colloidal silica, magnesium silicate and calcium silicate; or a mass percentage of the lubricant in the pharmaceutical composition is 0 wt % to 5 wt % excluding 0 wt %;

or, when the pharmaceutical composition further comprises a diluent, then the diluent is mannitol or lactose monohydrate; or a mass percentage of the diluent in the pharmaceutical composition is 0 wt % to 40 wt % excluding 0 wt %.

16. The pharmaceutical composition containing dabigatran etexilate as defined in claim 7, wherein, when the pharmaceutical composition exists in the form of powder, then a mass fraction of ethanol in the ethanol aqueous solution is 90% to 95%; or, in the powder, the active pharmaceutical ingredient existing in a molecular dispersion form or an amorphous form accounts for 15 wt % to 100 wt % of total mass of the active pharmaceutical ingredient;

or, when the pharmaceutical composition exists in the form of the neutral-core pellet, then in the neutral-core pellet, the active pharmaceutical ingredient existing in a molecular dispersion form or an amorphous form accounts for 15 wt % to 100 wt % of total mass of the active pharmaceutical ingredient; or, the neutral core is microcrystalline cellulose core or sugar spheres;

or, when the pharmaceutical composition exists in the form of the neutral-core pellet, then the neutral-core pellet comprises the components of following mass fraction: 12% to 30% of the active pharmaceutical ingredient, 6% to 24% of the amphiphilic polymer, 15% to 42% of the hydrophilic polymer and 33% to 50% of the neutral cores; or, the neutral-core pellet comprises the components of following mass fraction: 12% to 30% of dabigatran etexilate mesylate, 6% to 24% of polyvinyl caprolactam-polyvinyl acetate-polyethylene glycol graft copolymer, 15% to 42% of polyoxyethylene-polyoxypropylene glycol block copolymer P407 and 33% to 50% of sugar spheres; or, the neutral-core pellet comprises the components of following mass fraction: 13.3% to 24% of the active pharmaceutical ingredient, 3.33% to 28.27% of the amphiphilic polymer, 16.7% to 36% of the hydrophilic polymer and 40% to 66.7% of the neutral core; or, the neutral-core pellet comprises the components of following mass fraction: 13.3% to 24% of dabigatran etexilate mesylate, 3.33% to 28.27% of polyvinyl caprolactam-polyvinyl acetate-polyethylene glycol graft copolymer, 16.7% to 36% of polyoxyethylene-polyoxypropylene glycol block copolymer P407 and 40% to 66.7% of sugar spheres;

or, when the pharmaceutical composition exists in the form of the neutral-core pellet, then the pharmaceutical composition is composed of the components of following mass fraction: 18% of dabigatran etexilate mesylate, 6% of polyvinyl caprolactam-polyvinyl acetate-polyethylene glycol graft copolymer, 36% of polyoxyethylene-polyoxypropylene glycol block copolymer P407 and 40% of sugar spheres; or the pharmaceutical composition is composed of the components of following mass fraction: 24% of dabigatran etexilate mesylate, 6% of polyvinyl caprolactam-polyvinyl acetate-polyethylene glycol graft copolymer, 30% of polyoxyethylene-polyoxypropylene glycol block copolymer P407 and 40% of sugar spheres; or, the pharmaceutical composition is composed of the components of following mass fraction: 13.3% of dabigatran etexilate mesylate, 3.33% of polyvinyl caprolactam-polyvinyl acetate-polyethylene glycol graft copolymer, 16.7% of polyoxyethylene-polyoxypropylene glycol block copolymer P407 and 66.7% of sugar spheres;

or, when the pharmaceutical composition exists in the form of the neutral-core pellet, then in a method for preparing the neutral-core pellet comprises following steps, a mass fraction of ethanol in the ethanol aqueous solution is 90% to 95%;

or, when the pharmaceutical composition exists in the form of an acid-core pellet, then the acid core is tartaric acid core; or, a mass percentage of the acid core in the acid-core pellet is 17% to 36%;

or, when the pharmaceutical composition exists in the form of an acid-core pellet, then a mass percentage of the polyvinyl caprolactam-polyvinyl acetate-polyethylene glycol graft copolymer of the isolation layer in the acid-core pellet is 9% to 13%; a mass percentage of polyoxyethylene-polyoxypropylene glycol block copolymer P407 in the isolation layers in the acid-core pellet is 4% to 6%;

or, when the pharmaceutical composition exists in the form of an acid-core pellet, then the drug layer comprises the active pharmaceutical ingredient, polyvinyl caprolactam-polyvinyl acetate-polyethylene glycol graft copolymer and polyoxyethylene-polyoxypropylene glycol block copolymer P407, a mass percentage of the active pharmaceutical ingredient in the drug layer in the acid-core pellet is 14% to 19%, a mass percentage of polyvinyl caprolactam-polyvinyl acetate-polyethylene glycol graft copolymer in the drug layer in the acid-core pellet is 12% to 17%, and a mass percentage of polyoxyethylene-polyoxypropylene glycol block copolymer P407 in the drug layer in the acid-core pellet is 22% to 29%;

or, when the pharmaceutical composition exists in the form of an acid-core pellet, then the mass percentage of the acid core in the acid-core pellet is 17% to 36%; the mass percentage of polyvinyl caprolactam-polyvinyl acetate-polyethylene glycol graft copolymer in the isolation layer in the acid-core pellet is 9% to 13%, and the mass percentage of polyoxyethylene-polyoxypropylene glycol block copolymer P407 in the isolation layer in the acid-core pellet is 4% to 6%; the drug layer comprises the active pharmaceutical ingredient, polyvinyl caprolactam-polyvinyl acetate-polyethylene glycol graft copolymer and polyoxyethylene-polyoxypropylene glycol block copolymer P407, the mass percentage of the active pharmaceutical ingredient in the drug layer in the acid-core pellet is 14% to 19%, the mass percentage of polyvinyl caprolactam-polyvinyl acetate-polyethylene glycol graft copolymer in the drug layer in the acid-core pellet is 12% to 17%, and the mass percentage of polyoxyethylene-polyoxypropylene glycol block copolymer P407 in the drug layer in the acid-core pellet is 22% to 29%;

or, when the pharmaceutical composition exists in the form of an acid-core pellet, then the mass percentage of the acid core in the acid-core pellet is 35.7%; the mass percentage of polyvinyl caprolactam-polyvinyl acetate-polyethylene glycol graft copolymer in the isolation layer in the acid-core pellet is 9.6%, and the mass percentage of polyoxyethylene-polyoxypropylene glycol block copolymer P407 in the isolation layer in the acid-core pellet is 4.7%; the drug layer comprises the active pharmaceutical ingredient, polyvinyl caprolactam-polyvinyl acetate-polyethylene glycol graft copolymer and polyoxyethylene-polyoxypropylene glycol block copolymer P407, the mass percentage of the active pharmaceutical ingredient in the drug layer in the acid-core pellet is 14.4%, the mass percentage of polyvinyl caprolactam-polyvinyl acetate-polyethylene glycol graft copolymer in the drug layer in the acid-core pellet is 12.9%, and the mass percentage of polyoxyethylene-polyoxypropylene glycol block copolymer P407 in the drug layer in the acid-core pellet is 22.6%;

or, when the pharmaceutical composition exists in the form of granules, and the method for preparing the granules is wet granulation, then the a solvent adopted in the wet granulation is isopropanol;

or when the pharmaceutical composition exists in the form of granules, a method for preparing the granules is hot melting granulation.

17. The pharmaceutical composition containing dabigatran etexilate as defined in claim 10, wherein, the solid granule comprises the components of following mass fraction: 40% to 50% of polyvinyl caprolactam-polyvinyl acetate-polyethylene glycol graft copolymer, 0% to 55% of lactose, 5% to 20% of croscarmellose sodium, 0% to 5% of silica and 0% to 2% of magnesium stearate;

or, the solid granule comprises the components of following mass fraction: 40% to 50% of polyvinyl caprolactam-polyvinyl acetate-polyethylene glycol graft copolymer, 0% to 55% of polyoxyethylene-polyoxypropylene glycol block copolymer P407, 5% to 20% of croscarmellose sodium, 0% to 5% of silica and 0% to 2% of magnesium stearate;

or, the solid granule comprises the components of following mass fraction: 41% to 58% of polyvinyl caprolactam-polyvinyl acetate-polyethylene glycol graft copolymer, 3% to 33% of mannitol, 13% to 26% of polyoxyethylene-polyoxypropylene glycol block copolymer P407, 5% to 20% of croscarmellose sodium, 0% to 5% of silica and 0% to 2% of magnesium stearate;

or, the solid granule is composed of the components of following mass fraction: 41.88% of polyvinyl caprolactam-polyvinyl acetate-polyethylene glycol graft copolymer, 51.87% of lactose monohydrate, 5.25% of croscarmellose sodium, 0.5% of magnesium stearate and 0.5% of silica;

or, the solid granule is composed of the components of following mass fraction: 41.88% of polyvinyl caprolactam-polyvinyl acetate-polyethylene glycol graft copolymer, 51.87% of polyoxyethylene-polyoxypropylene glycol block copolymer P407, 5.25% of croscarmellose sodium, 0.5% of magnesium stearate and 0.5% of silica;

or, the solid granule is composed of the components of following mass fraction: 49.5% of polyvinyl caprolactam-polyvinyl acetate-polyethylene glycol graft copolymer, 24.7% of mannitol, 19.8% of polyoxyethylene-polyoxypropylene glycol block copolymer P407, 5.0% of croscarmellose sodium, 0.5% of magnesium stearate and 0.5% of silica;

or, a mass percentage of mass of the solid granule in total mass of the pharmaceutical composition is 9% to 35%.

18. The method for preparing the pharmaceutical composition as defined in claim 12, wherein, when the pharmaceutical composition does not contain a neutral core and exists in a form of powder, a mass fraction of ethanol in the ethanol aqueous solution is 90% to 95%;

when the pharmaceutical composition contains a neutral core and exists in a form of a neutral-core pellet, moisture content of the pre-dried neutral cores is lower than 1.0 wt %; or, the organic solvent is an ethanol solution; or, a mass fraction of ethanol in the ethanol aqueous solution is 90% to 95%; or, a mass percentage of the pharmaceutical composition in the coating solution is 20% to 24%; or, in the spraying process, an inlet temperature of air is 45 to 60° C.; or, in the spraying process, a temperature of the granule is 30 to 50° C.; and after spraying is finished, the granule is dried till moisture content is lower than 1.0 wt %;

when the pharmaceutical composition contains an acid core and exists in a form of an acid-core pellet, in step (1), moisture content of the pre-dried acid core is lower than 1.0 wt %; or, in step (1), the organic solvent is an ethanol aqueous solution; or, a mass fraction of ethanol in the ethanol aqueous solution is 90% to 95%; or, in step (1), a mass percentage of the pharmaceutical composition in the coating solution is 20% to 26%; or, in step (1), in the spraying process, an inlet temperature of air is 45 to 60° C.; or, in step (1), in the spraying process, a temperature of the acid granules is 30 to 32° C.; or, in step (1), after spraying is finished, the acid granule is dried till moisture content is lower than 1.0 wt %; or, in step (2), the organic solvent is an ethanol solution; or, a mass fraction of ethanol in the ethanol aqueous solution is 90% to 95%; or, in step (2), a mass percentage of the pharmaceutical composition in the coating solution is 20% to 24%; or, in step (2), in the spraying process, an inlet temperature of air is 45 to 60° C.; or, in step (2), in the spraying process, a temperature of the acid-core pellets is 30 to 32° C.; or, in step (2), after spraying is finished, the acid-core pellet is dried till moisture content is lower than 1.0 wt %.

* * * * *